US011471339B2

(12) United States Patent
Ishikawa

(10) Patent No.: US 11,471,339 B2
(45) Date of Patent: Oct. 18, 2022

(54) UNDERPANTS-TYPE DISPOSABLE DIAPER

(71) Applicant: Daio Paper Corporation, Ehime (JP)

(72) Inventor: Yoshitake Ishikawa, Ehime (JP)

(73) Assignee: Daio Paper Corporation, Ehime (JP)

( * ) Notice: Subject to any disclaimer, the term of this patent is extended or adjusted under 35 U.S.C. 154(b) by 313 days.

(21) Appl. No.: 16/632,225

(22) PCT Filed: Aug. 31, 2018

(86) PCT No.: PCT/JP2018/032380
§ 371 (c)(1),
(2) Date: Jan. 17, 2020

(87) PCT Pub. No.: WO2019/065081
PCT Pub. Date: Apr. 4, 2019

(65) Prior Publication Data
US 2020/0214906 A1    Jul. 9, 2020

(30) Foreign Application Priority Data

Sep. 27, 2017 (JP) .............................. JP2017-187204

(51) Int. Cl.
*A61F 13/494* (2006.01)
*A61F 13/496* (2006.01)
*A61F 13/49* (2006.01)

(52) U.S. Cl.
CPC .... *A61F 13/49413* (2013.01); *A61F 13/4963* (2013.01); *A61F 2013/4948* (2013.01); *A61F 2013/49093* (2013.01)

(58) Field of Classification Search
CPC ............ A61F 13/49413; A61F 13/4963; A61F 13/49; A61F 13/494; A61F 13/4942;
(Continued)

(56) References Cited

U.S. PATENT DOCUMENTS

2005/0103436 A1   5/2005   Otsubo et al.
2006/0030831 A1   2/2006   Matsuda et al.
2012/0283682 A1   11/2012  Otsubo et al.

FOREIGN PATENT DOCUMENTS

EP    1626690    2/2006
EP    3357465    8/2018
(Continued)

OTHER PUBLICATIONS

International Search Report for PCT/JP2018/032380, dated Oct. 23, 2018.

*Primary Examiner* — Nicholas J. Weiss
*Assistant Examiner* — Gabriella E Burnette
(74) *Attorney, Agent, or Firm* — Andrus Intellectual Property Law, LLP

(57) ABSTRACT

The rising gather of a disposable diaper includes: a main unit portion having a first portion extending from both sides of an inner member toward the center in the width direction and a second portion extending outward in the width direction. Front and back fallen portions are formed by fixing front and back end portions in the main unit portion to the inner member. The front and back fallen portions have a protruding portion in which the second portion protrudes 5 to 40 mm outward in the width direction than a side edge of the first portion. The protruding portion of the front fallen portion has a protruding fixing portion fixed to the front outer member overlapping with a back surface side thereof. The protruding portion of the back fallen portion has a protruding fixing portion fixed to the back outer member overlapping with a back surface side thereof.

17 Claims, 12 Drawing Sheets

(58) Field of Classification Search
CPC .............. A61F 13/49446; A61F 13/496; A61F 2013/4948; A61F 2013/49093; A61F 2013/49433; A61F 2013/49493; A61F 2013/49092
See application file for complete search history.

(56) References Cited

FOREIGN PATENT DOCUMENTS

| | | |
|---|---|---|
| JP | 2004-073428 | 3/2004 |
| JP | 2006-525857 | 11/2006 |
| JP | 4964993 | 5/2011 |
| JP | 2011-147516 | 8/2011 |
| JP | 2014-028308 | 2/2014 |
| JP | 2015-092947 | 5/2015 |
| JP | 2017-113347 | 6/2017 |
| WO | WO-2017110150 A1 * | 6/2017 ............. A61F 13/49 |

* cited by examiner

[FIG.1]
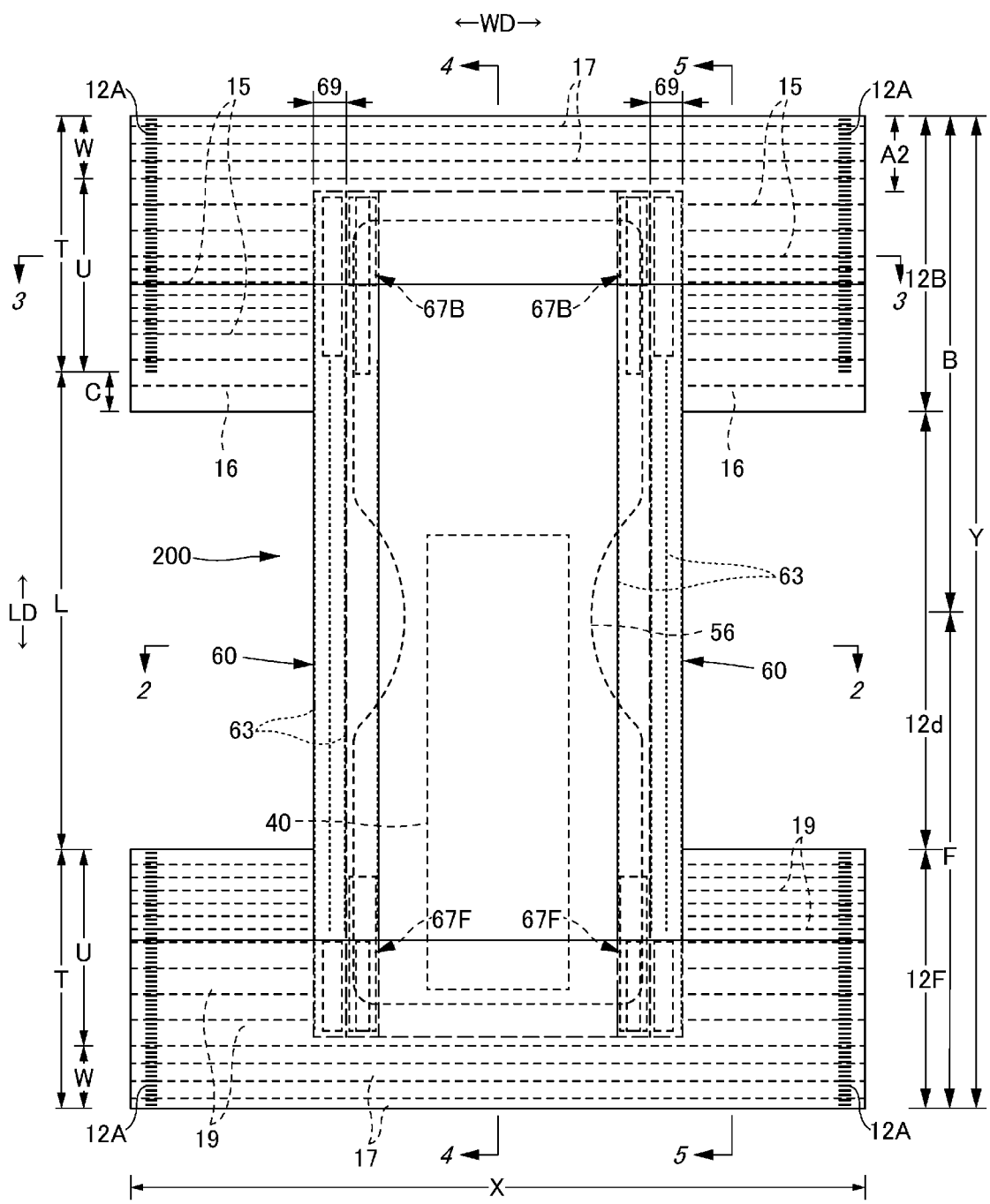

[FIG.2]
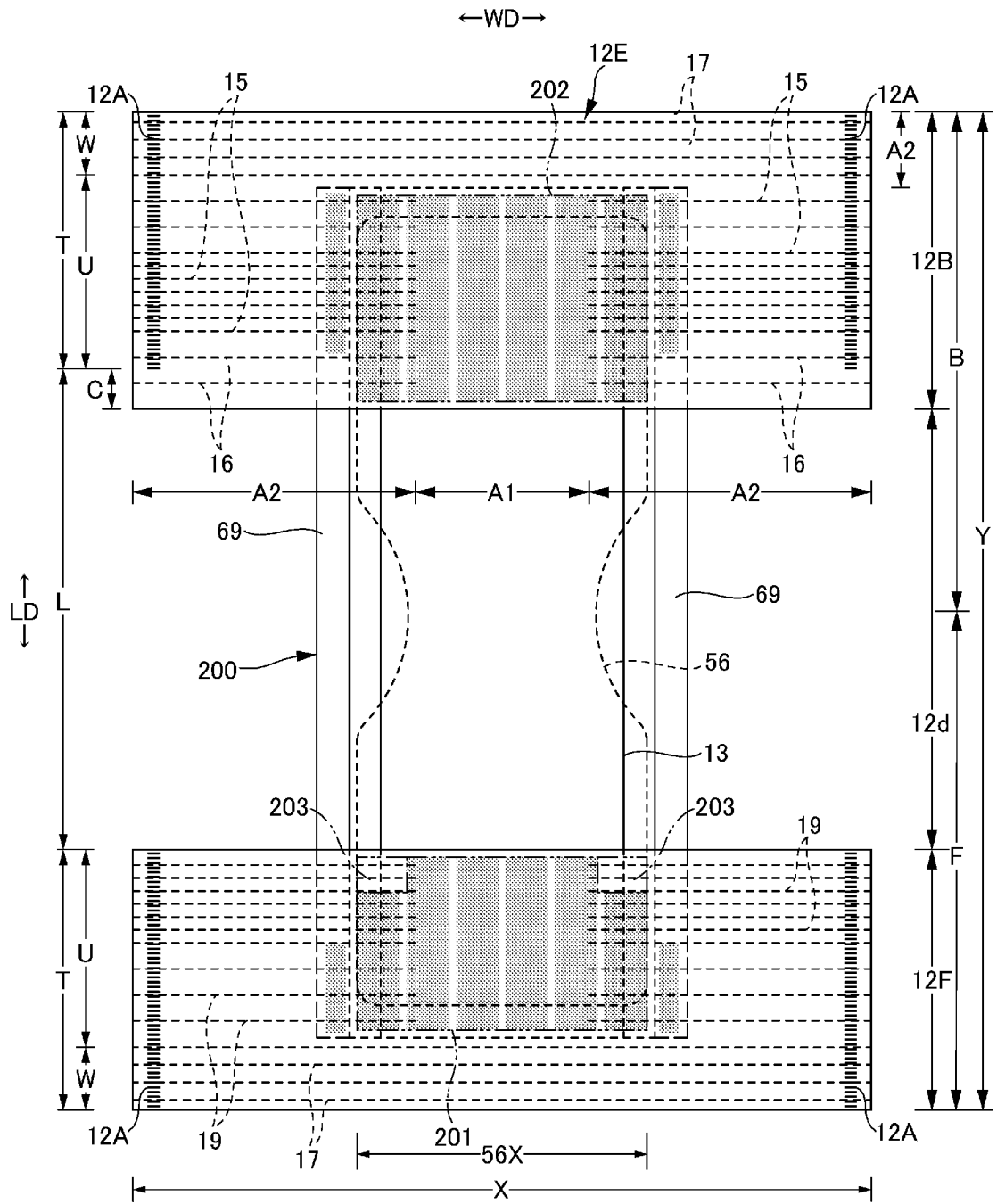

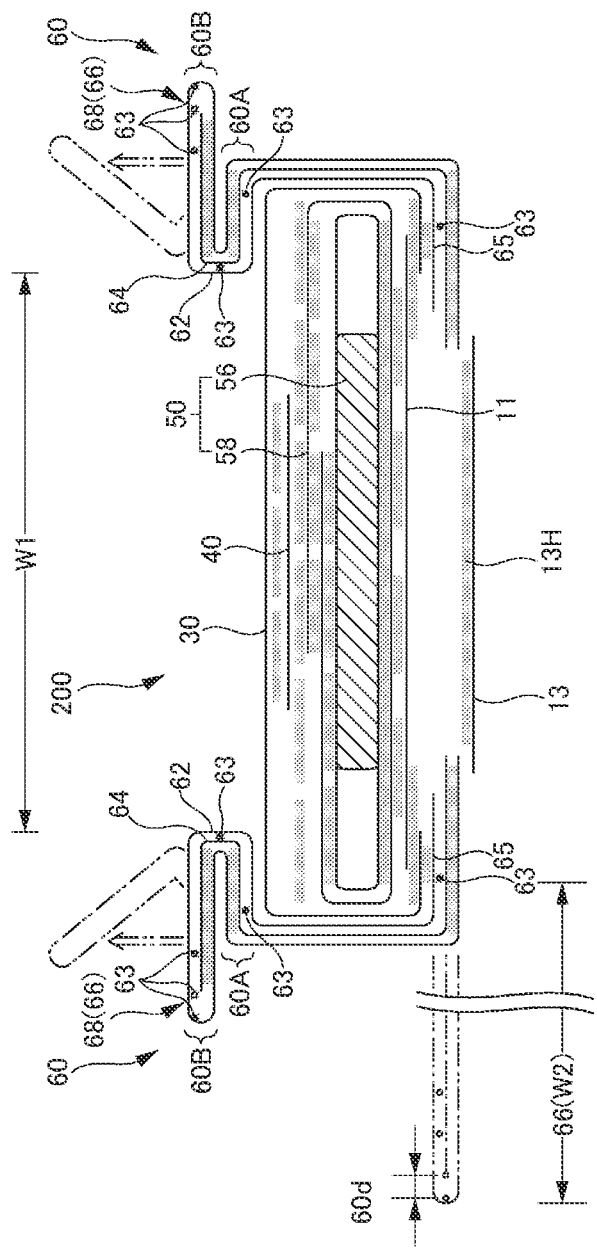
[FIG. 3]

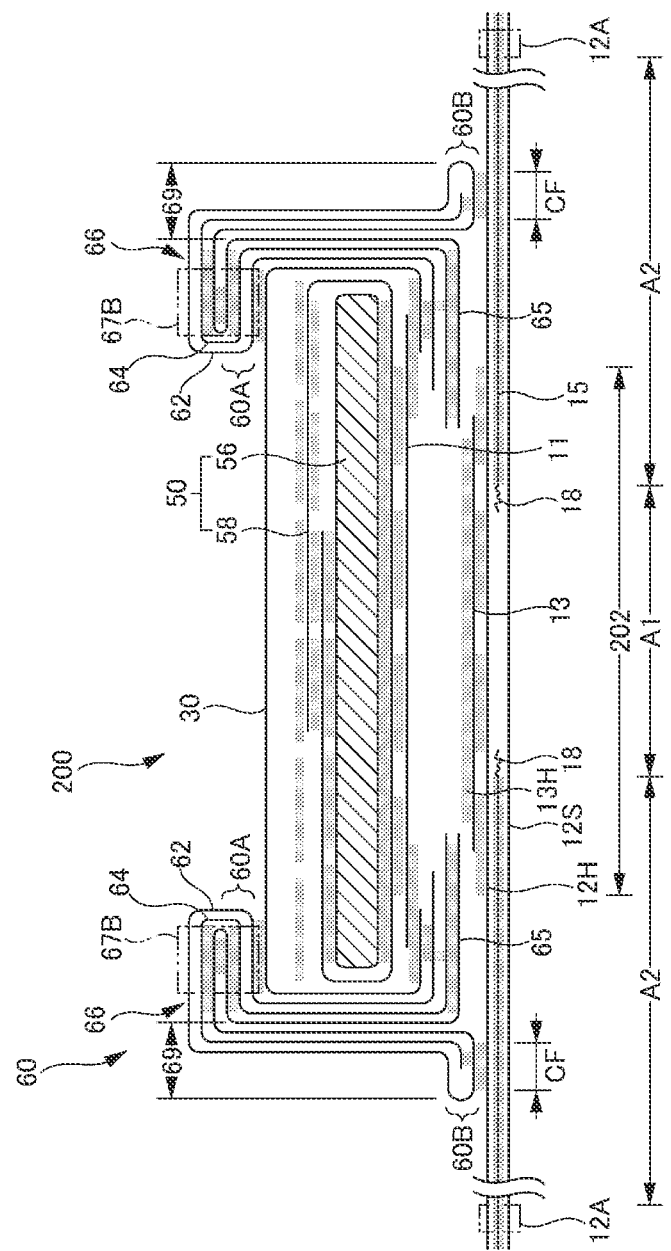
[FIG. 4]

[FIG.5]
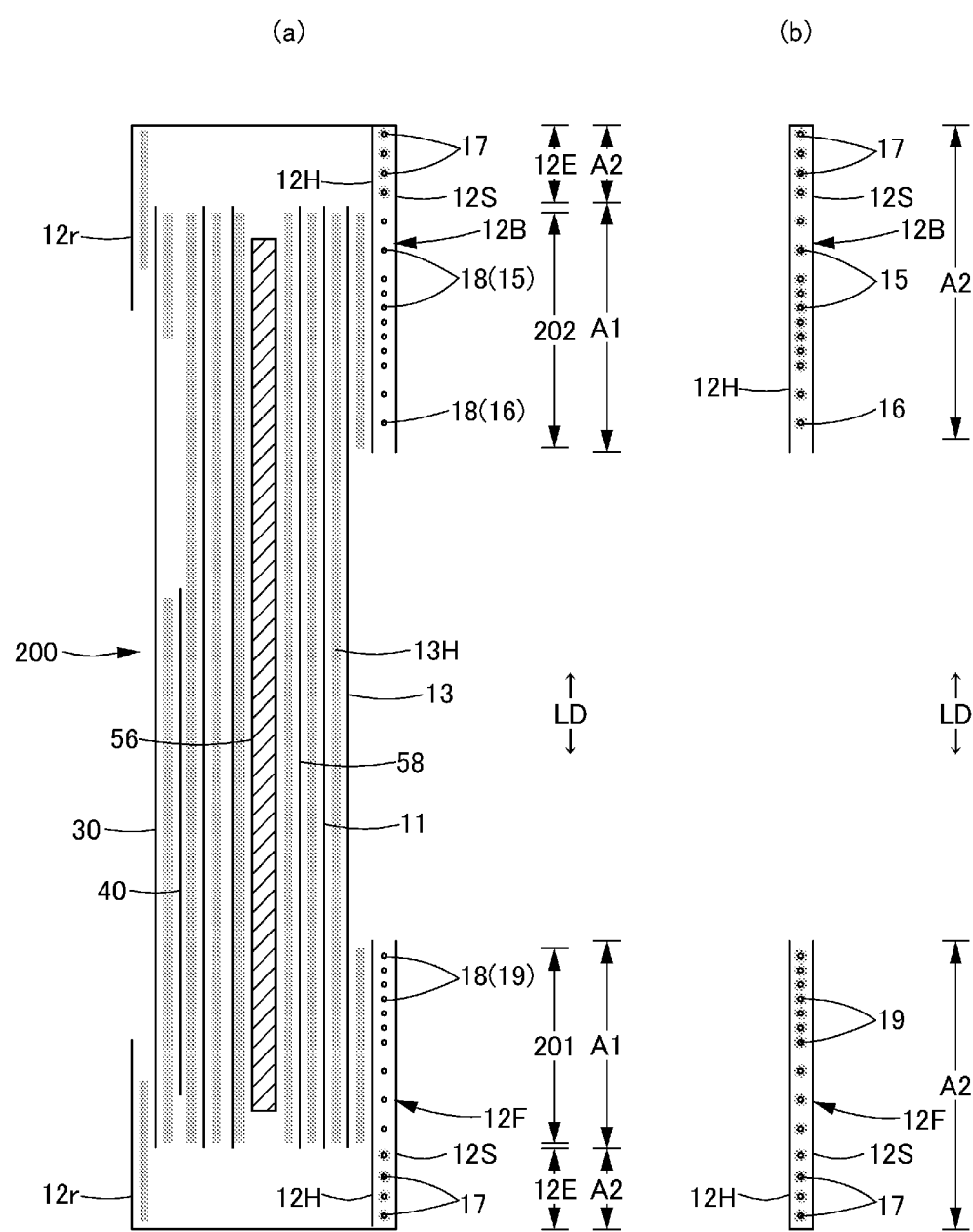

[FIG.6]
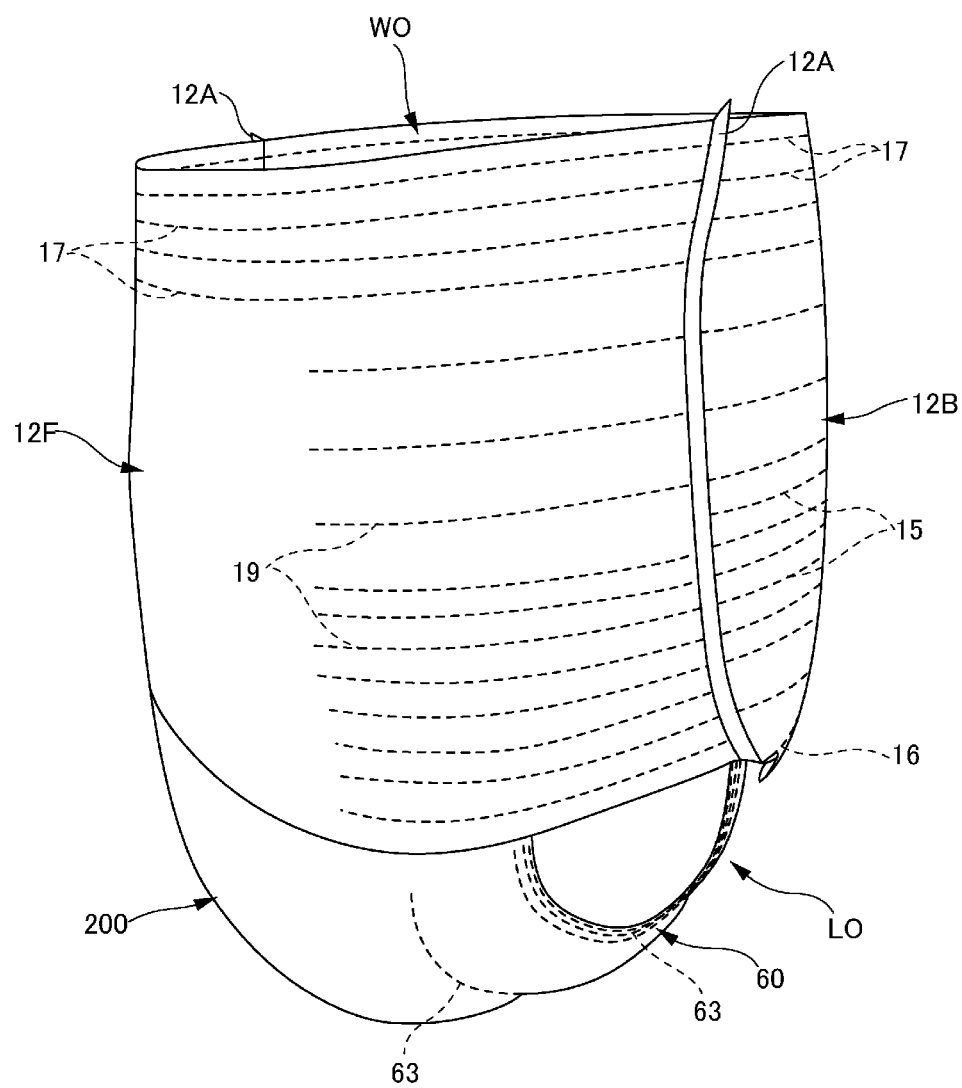

[FIG.7]
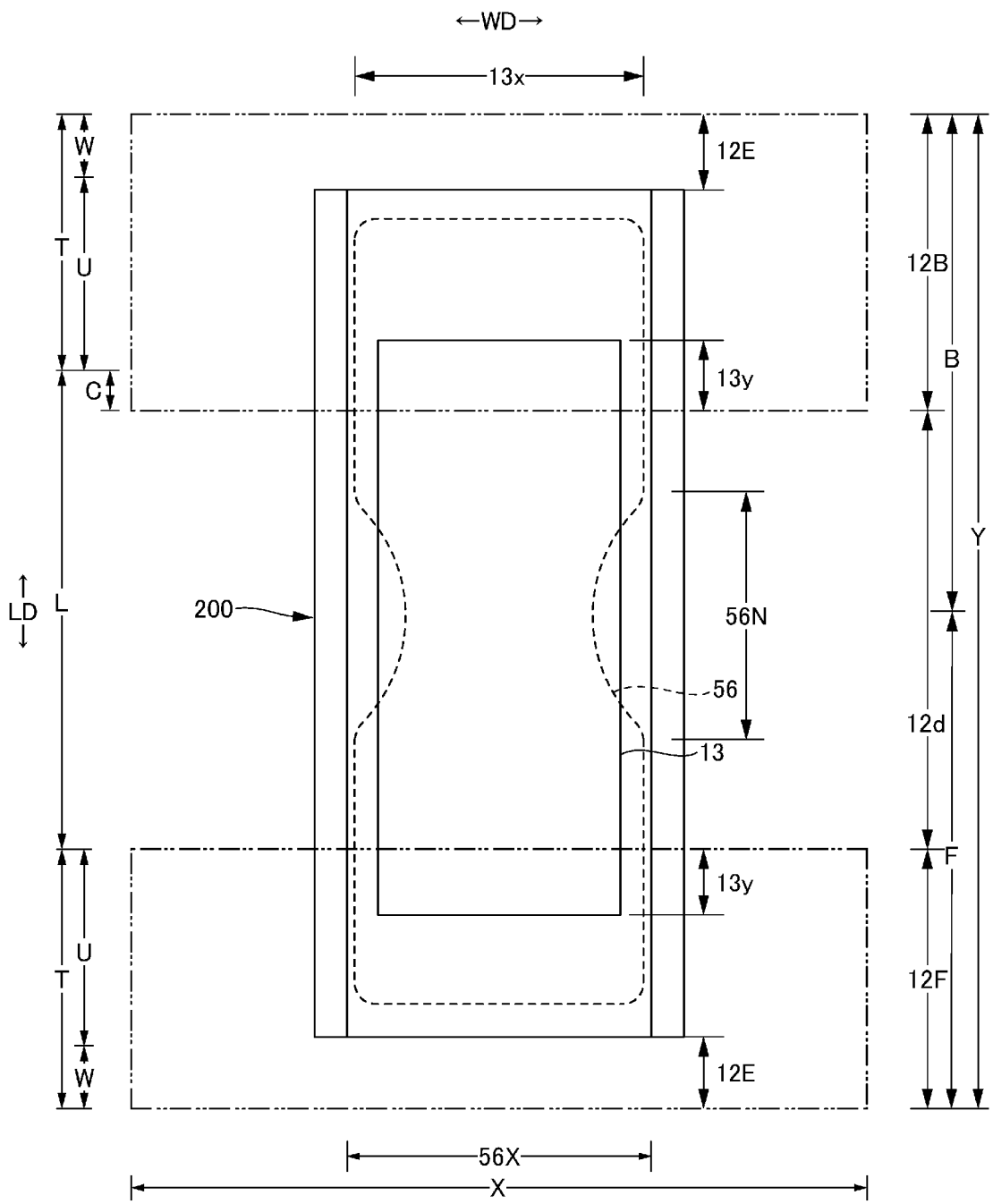

[FIG. 8]
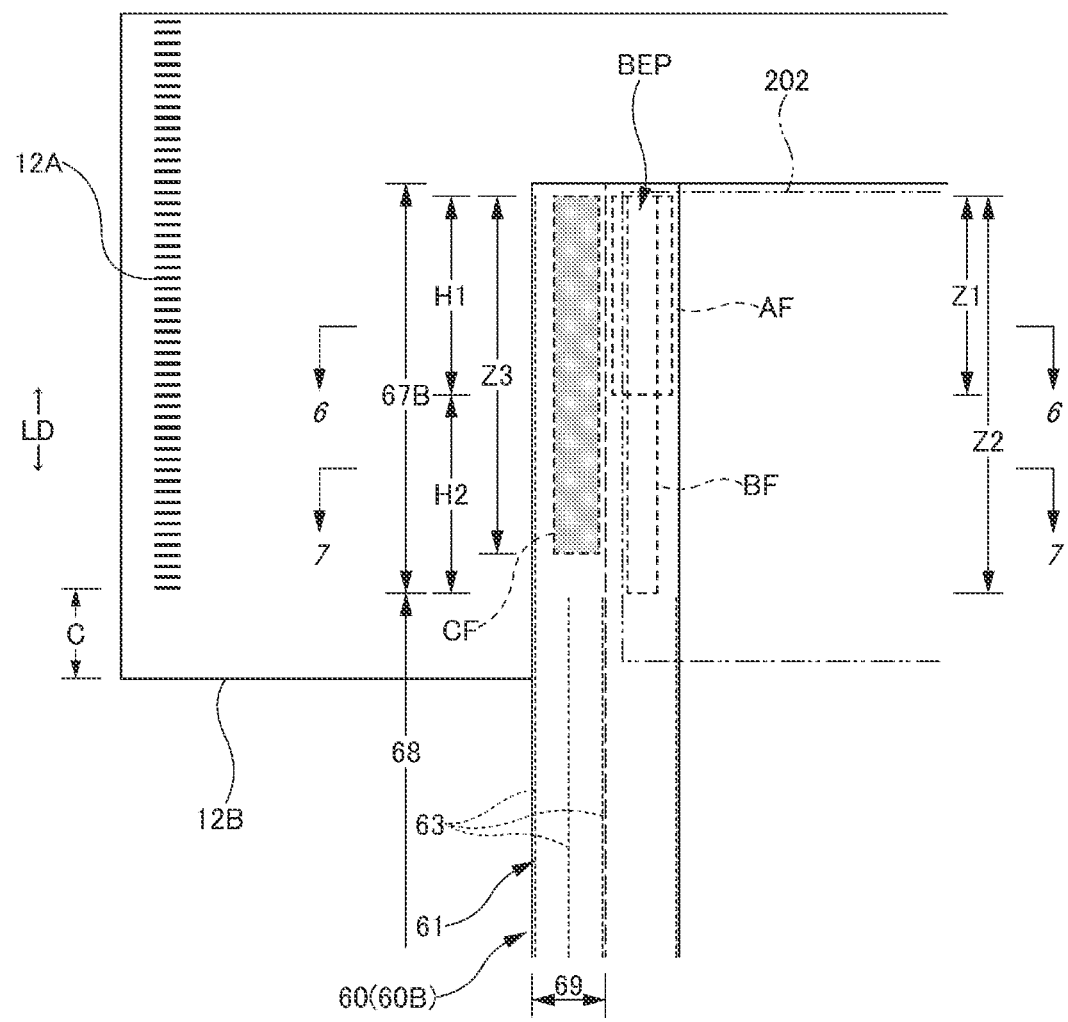

[FIG. 9]
(a)
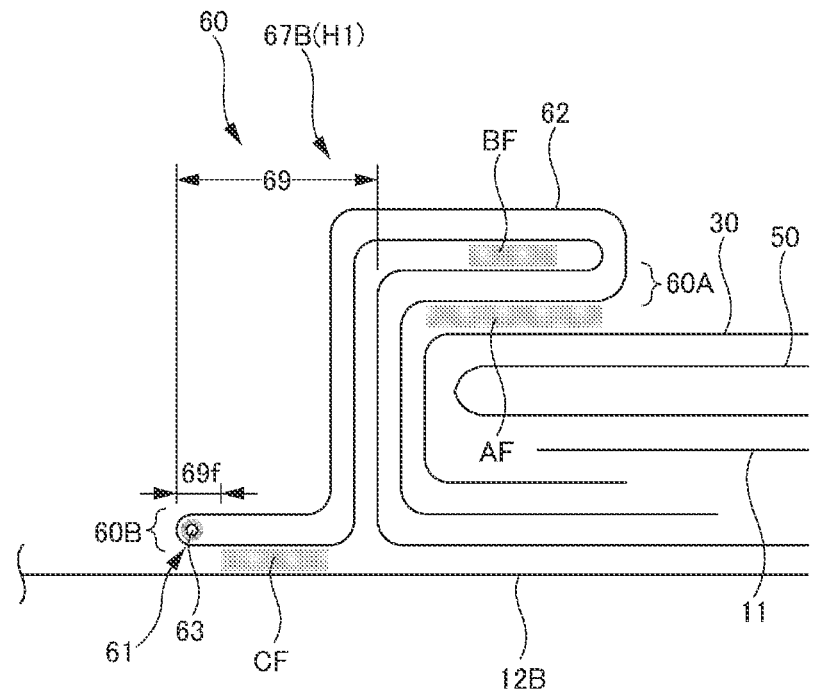
(b)
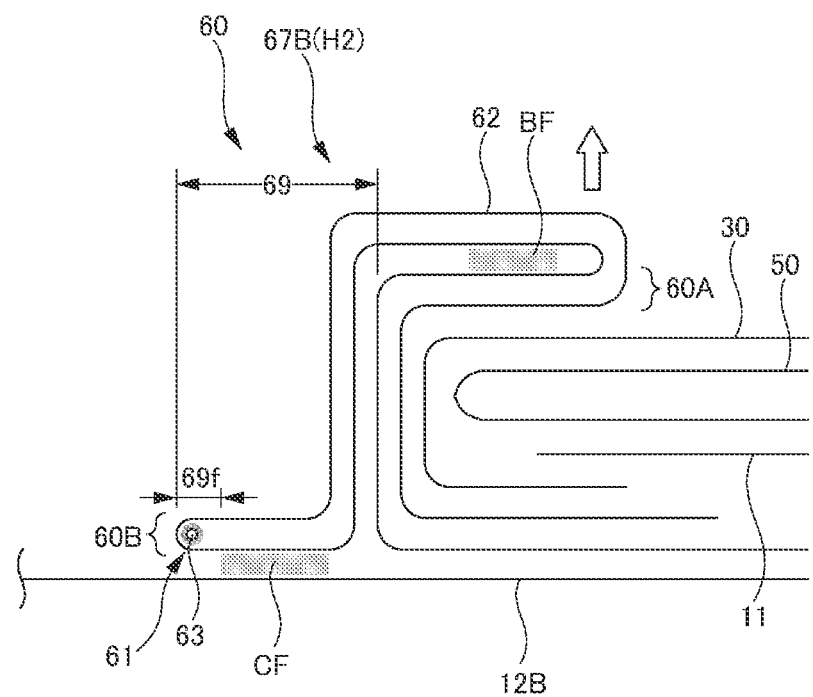

[FIG. 10]
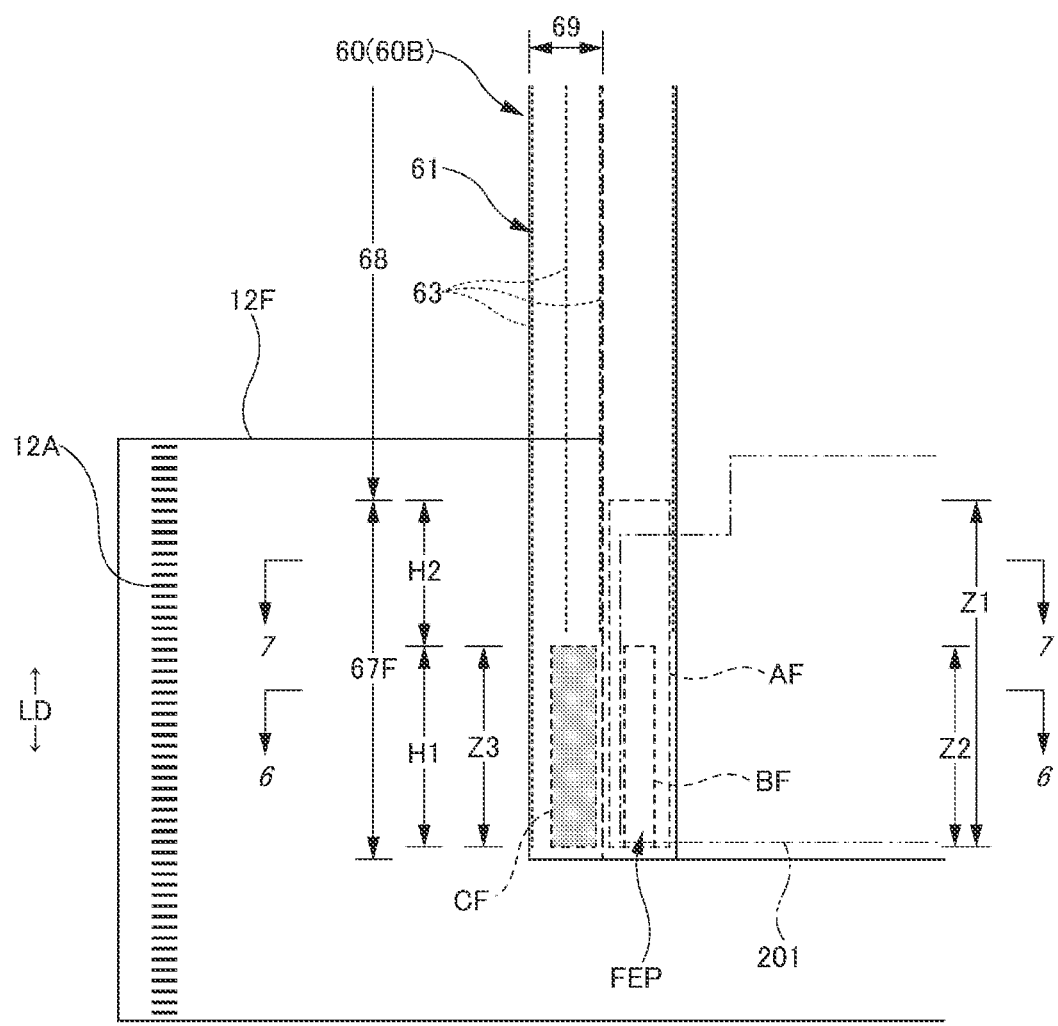

[FIG. 11]
(a)
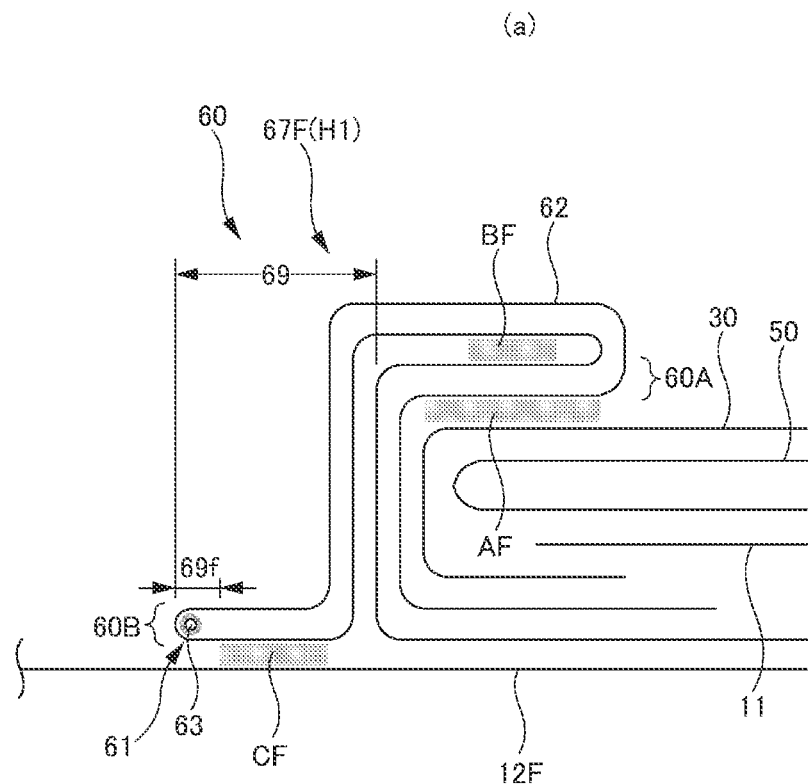
(b)
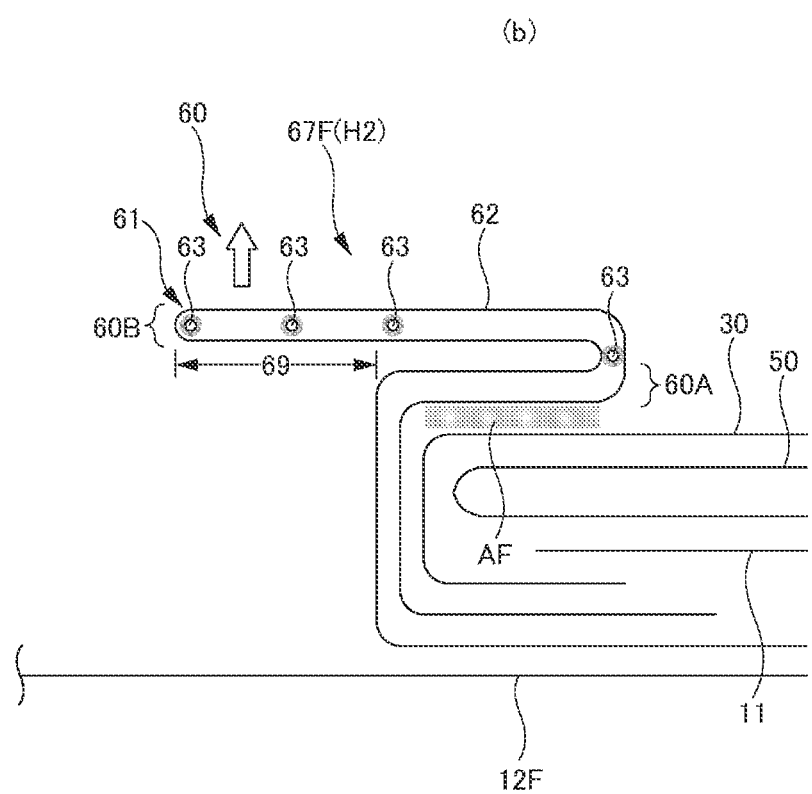

[FIG. 12]
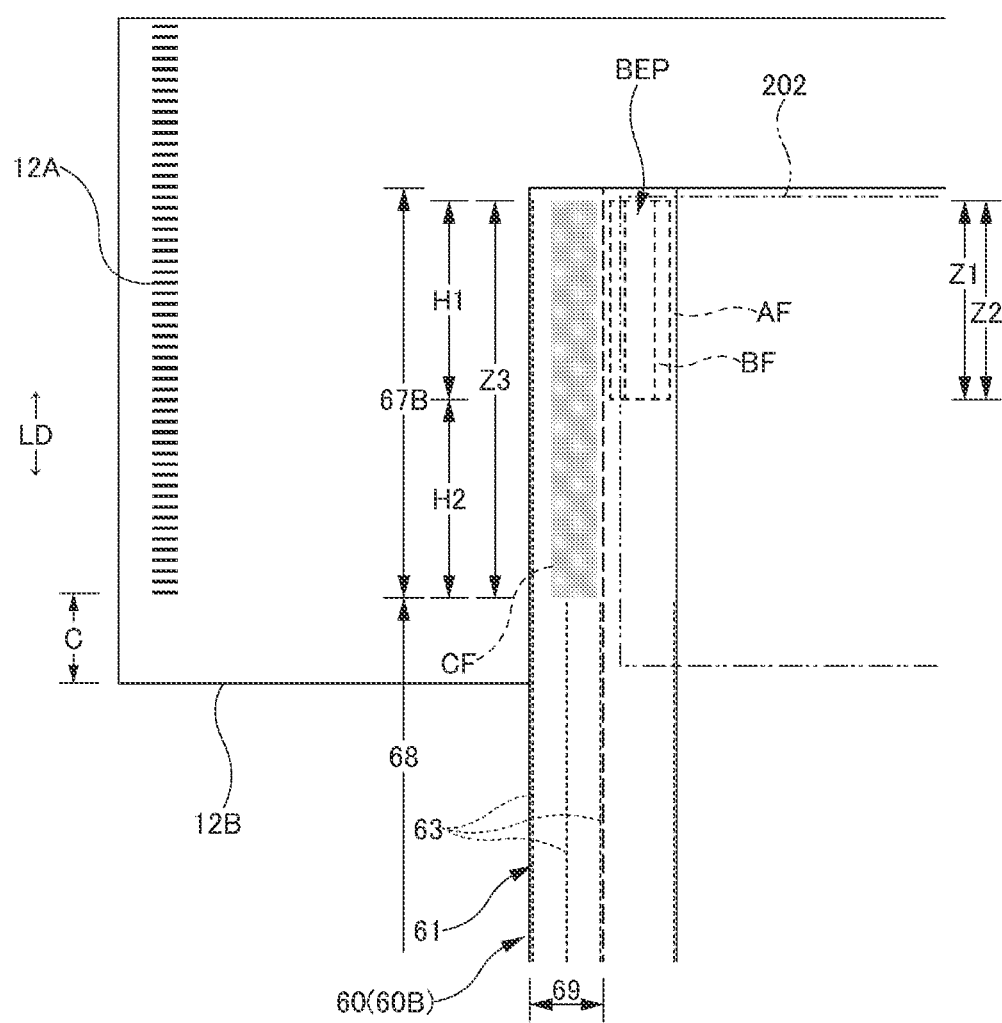

UNDERPANTS-TYPE DISPOSABLE DIAPER

CROSS-REFERENCE TO RELATED APPLICATIONS

This application is the U.S. national stage application of International Application PCT/JP2018/032380, filed Aug. 31, 2018, which international application was published on Apr. 4, 2019, as International Publication WO 2019/065081 in the Japanese language. The International Application claims priority of Japanese Patent Application No. 2017-187204, filed Sep. 27, 2017. The international application and Japanese application are both incorporated herein by reference, in entirety.

TECHNICAL FIELD

The present invention relates to an underpants-type disposable diaper.

BACKGROUND ART

As a form of an underpants-type disposable diaper, an outer member separated type underpants-type disposable diaper is known (see, for example, Patent Literatures 1 to 6). The outer member separated type underpants-type disposable diaper includes a front outer member forming at least a lower torso portion of a front body and a back outer member forming at least a lower torso portion of a back body independently. The front outer member and the back outer member are separated from each other in a front-back direction. An inner member including an absorber is attached so as to extend from the front outer member to the back outer member. Both sides of the front outer member and both sides of the back outer member are bonded to each other to form a side seal portion, and a waist opening and a pair of left and right leg openings are thereby formed. Such an outer member separated type diaper has an advantage that the outer member does not have to be cut off, or only a small area needs to be cut off even if the outer member is cut off in order to form a leg opening. That is, separated pieces (trims) are discarded, and therefore waste of the material (trim loss) can be suppressed advantageously.

In order to prevent so-called side leakage, an underpants-type disposable diaper generally has a rising gather that rises from a surface to both sides of an inner member in a width direction. The rising gather has various structures, but many rising gathers have the following basic structure. That is, many rising gathers each include: a root portion fixed to a disposable wearing article; a main unit portion extending from the root portion; a front fallen portion formed by fixing a front end portion of the main unit portion in a state of falling down; a back fallen portion formed by fixing a back end portion of the main unit portion in a state of falling down; a non-fixed rising portion located between the front fallen portion and the back fallen portion in the main unit portion; and a gather elastic member attached to at least a tip portion of the rising portion in a front-back direction.

However, in an outer member separated type underpants-type disposable diaper, an edge of an outer member on a leg opening side has a linear shape in a width direction or a shape similar thereto, and intersects with a side edge of an inner member at a right angle or an angle close thereto. Therefore, in a conventional rising gather, it is difficult to cover a gluteal region and an inguinal portion (partially protrudes or is exposed) disadvantageously.

CITATION LIST

Patent Literature

Patent Literature 1: JP 2004-073428 A
Patent Literature 2: JP 2006-525857 A
Patent Literature 3: JP 2011-147516 A
Patent Literature 4: JP 2014-028308 A
Patent Literature 5: JP: 4964993 B2
Patent Literature 6: JP 2015-092947 A

SUMMARY OF INVENTION

Technical Problem

Therefore, a main object of the present invention is, for example, to improve a covering property of a gluteal region and an inguinal portion in the outer member separated type underpants-type disposable diaper.

Solution to Problem

Various aspects of the underpants-type disposable diaper which have solved the problem are as follows.

First Aspect

An underpants-type disposable diaper including: a front outer member forming at least a lower torso portion of a front body and a back outer member forming at least a lower torso portion of a back body independently, the front outer member and the back outer member being separated from each other in a front-back direction;

an inner member including an absorber extending in the front-back direction from the front outer member to the back outer member, and being bonded to the front outer member and the back outer member; and a side seal portion to which both sides of the front outer member and both sides of the back outer member are bonded to form a waist opening and a pair of left and right leg openings, the inner member including raising gathers that rise from both sides, the rising gathers each including: a main unit portion having a first portion extending from both sides of a surface of the inner member toward the center in the width direction and a second portion extending from a tip of the first portion outward in the width direction; a front fallen portion and a back fallen portion formed by fixing a front end portion and a back end portion in the main unit portion to a surface of the inner member in a state of falling down, respectively; a non-fixed rising portion located between the front fallen portion and the back fallen portion; and a gather elastic member attached to at least a tip portion of the rising portion in the front-back direction, wherein each of the front fallen portion and the back fallen portion has a protruding portion in which the second portion protrudes 5 to 40 mm outward in the width direction than a side edge of the first portion, and the protruding portion of the front fallen portion has a protruding fixing portion fixed to the front outer member overlapping with a back surface side thereof, and the protruding portion of the back fallen portion has a protruding fixing portion fixed to the back outer member overlapping with a back surface side thereof.

Action and Effect

In the underpants-type disposable diaper according to the present aspect, the width of the inner member is narrowed by rise of the rising portion of the rising gather at a front-back direction intermediate portion of the inner member in a wearing state. However, by disposing protruding portions fixed to the front outer member and the back outer member in the second portions of the front fallen portion and the back fallen portion, the width of the inner member is increased as the inner member goes toward front and back both sides thereof. Therefore, despite of the outer member separated type disposable diaper, a covering property of the vicinity of a corner portion formed by an edge on the leg opening side of each of the front outer member and the back outer member and a side edge of the inner member, that is, a covering property of a gluteal region and an inguinal portion is improved.

Second Aspect

The underpants-type disposable diaper according to the first aspect, in which the front fallen portion and the back fallen portion each have a first fixing portion in which the first portion is bonded to a surface of the inner member, and a second fixing portion in which the second portion is bonded to the first portion, the back fallen portion has a full fallen region having the first fixing portion and the second fixing portion on a back side, and has a half fallen region not having the first fixing portion and having the second fixing portion on a front side, and the front-back direction size of the second fixing portion is twice or more the front-back direction size of the first fixing portion, and the front fallen portion has a full fallen region having the first fixing portion and the second fixing portion on a front side, and has a half fallen region not having the second fixing portion and having the first fixing portion on a back side.

Action and Effect

As in the present aspect, by disposing the half fallen region having only the second fixing portion on the front side of the back fallen portion, the second portion does not easily fall inward in the width direction. Therefore, an upper surface fits well to a surface of a gluteal region, and hardly bites into an intergluteal cleft. In addition, the half fallen region of the back fallen portion comes into contact with a bulging portion of the buttock. Therefore, even if the second portion is bonded to the first portion, there is no risk that a gap may be generated between the diaper and a body. In addition, by disposing the half fallen region having only the first fixing portion on the back side of the front fallen portion, the second portion firmly rises on the basis of the first portion fixed by the first fixing portion, and the diaper fits to a depression of an inguinal portion in a more stable posture. Therefore, this is preferable.

Third Aspect

The underpants-type disposable diaper according to the first or second aspect, in which the front fallen portion and the back fallen portion each have a first fixing portion in which the first portion is bonded to a surface of the inner member, and a second fixing portion in which the second portion is bonded to the first portion, the front-back direction size of the protruding fixing portion in the back fallen portion is 0.7 to 1 time the size of a longer one out of the front-back direction size of the first fixing portion and the front-back direction size of the second fixing portion located on a lateral side thereof, and the front-back direction size of the protruding fixing portion in the front fallen portion is 0.7 to 1 time the size of a shorter one out of the front-back direction size of the first fixing portion and the front-back direction size of the second fixing portion located on a lateral side thereof.

Action and Effect

By setting the front-back direction size of the protruding fixing portion within the range of the present aspect, a covering property of a gluteal region is improved, and the diaper fits to a depression of an inguinal portion in a more stable posture without depending on whether the front-back direction size of the first fixing portion is larger or smaller than that of the second fixing portion.

Fourth Aspect

The underpants-type disposable diaper according to the second or third aspect, in which a side edge portion of the protruding portion is a non-fixed free edge, a gather elastic member disposed at a tip portion of the rising portion extends to the free edge, and the free edge rises by contraction of the gather elastic member.

Action and Effect

As described above, it is practically difficult to fix even a side edge portion of the protruding portion to the front outer member and the back outer member. Therefore, it is also preferable to make the side edge portion of the protruding portion rise by the gather elastic member to enhance leakage prevention using this.

Fifth Aspect

The underpants-type disposable diaper according to any one of the first to fourth aspects, in which the front outer member and the back outer member each have a stretchable region that stretches and contracts in a width direction in a portion overlapping with the protruding portion, and the protruding fixing portion of the front fallen portion is fixed to the stretchable region of the front outer member, the protruding fixing portion of the back fallen portion is fixed to the stretchable region of the back outer member, and the protruding fixing portions are stretchable together with the stretchable regions.

Action and Effect

Before wearing, the protruding portion contracts together with the front outer member and the back outer member, and the leg opening becomes wider. Therefore, a hand or a foot easily passes through the leg opening during wearing work. Then, at the time of wearing, the protruding portion stretches and extends together with the front outer member and the back outer member, and a gluteal region and an inguinal portion are covered.

Sixth Aspect

The underpants-type disposable diaper according to the fifth aspects, in which the protruding fixing portion does not contract by contraction of the gather elastic member.

Action and Effect

When the protruding fixing portion is stretchable in the width direction together with the front outer member and the back outer member, if the protruding fixing portion is stretchable in the front-back direction by the gather elastic member, the protruding portion contracts in the width direction and the front-back direction and becomes like a hard bump in a wearing state. Therefore, a wearing feeling may be deteriorated. Therefore, it is desirable that the protruding fixing portion does not contract by contraction of the gather elastic member.

Seventh Aspect

The underpants-type disposable diaper according to any one of the first to sixth aspects, in which
the back fallen portion is disposed on a front edge of the back outer member or on a back side thereof, and the front fallen portion is disposed on a back edge of the front outer member or on a front side thereof.

Action and Effect

As described above, when the rising gather has a protruding portion, a problem that the rising portion falls inward hardly occurs. Therefore, the range of the rising portion is preferably widened in the front-back direction to increase fitting to a gluteal region and an inguinal portion.

Advantageous Effects of Invention

As described above, according to the present invention, a covering property of a gluteal region and an inguinal portion can be improved in an outer member separated type underpants-type disposable diaper advantageously, for example.

BRIEF DESCRIPTION OF DRAWINGS

FIG. 1 is a plan view illustrating an inner surface of an underpants-type disposable diaper in an unfolded state.
FIG. 2 is a plan view illustrating an outer surface of the underpants-type disposable diaper in an unfolded state.
FIG. 3 is a cross-sectional view cut along 2-2 of FIG. 1.
FIG. 4 is a cross-sectional view cut along 3-3 of FIG. 1.
FIG. 5(a) is a cross-sectional view cut along 4-4 of FIG. 1, and FIG. 5(b) is a cross-sectional view cut along 5-5 of FIG. 1.
FIG. 6 is a perspective view of the underpants-type disposable diaper.
FIG. 7 is a plan view illustrating a main part of the underpants-type disposable diaper.
FIG. 8 is a plan view illustrating a main part of a back side of the underpants-type disposable diaper in an unfolded state.
FIG. 9(a) is a cross-sectional view cut along 6-6 of FIG. 8, and FIG. 9(b) is a cross-sectional view cut along 7-7 of FIG. 8.
FIG. 10 is a plan view illustrating a main part of a front side of the underpants-type disposable diaper in an unfolded state.
FIG. 11(a) is a cross-sectional view cut along 6-6 of FIG. 10, and FIG. 11(b) is a cross-sectional view cut along 7-7 of FIG. 10.

FIG. 12 is a plan view illustrating a main part of a back side of the underpants-type disposable diaper in an unfolded state.

DESCRIPTION OF EMBODIMENTS

Hereinafter, an embodiment of the present invention will be described in detail with reference to the attached drawings. A dotted pattern portion in the cross-sectional views illustrates an adhesive as a bonding means for bonding constituent members located on a front surface side and a back surface side, and is formed by applying a hot melt adhesive by solid application, bead application, curtain application, summit application, spiral application, pattern coating (transfer of a hot melt adhesive by a letterpress method), or the like. A fixing portion of an elastic member is formed, instead of this or in addition to this, by application to an outer peripheral surface of an elastic member by a comb gun, SureWrap application, or the like. Examples of the hot melt adhesive include an EVA-based agent, a pressure-sensitive rubber-based agent (elastomer-based agent), an olefin-based agent, and a polyester/polyamide-based agent, and these can be used without particular limitation. As a bonding means for bonding constituent members, a means by material welding such as heat sealing or ultrasonic sealing can also be used.

FIGS. 1 to 11 illustrate an example of an underpants-type disposable diaper. The underpants-type disposable diaper includes: a front outer member 12F forming at least a lower torso portion of a front body F; a back outer member 12B forming at least a lower torso portion of a back body B; and an inner member 200 disposed inside the outer members 12F and 12B so as to extend from the front outer member 12F to the back outer member 12B through a crotch portion. Both sides of the front outer member 12F and both sides of the back outer member 12B are bonded to each other to form a side seal portion 12A. As a result, an opening formed by the front and back end portions of the outer members 12F and 12B is a waist opening WO through which a wearer's torso passes, and a portion surrounded by lower edges of the outer members 12F and 12B and a side edge of the inner member 200 on both sides of the inner member 200 in the width direction is a leg opening LO through which a leg passes. The inner member 200 is a portion for absorbing and holding excrement such as urine, and the outer members 12F and 12B are portions for supporting the inner member 200 with respect to the body of a wearer. A reference character Y represents the maximum length of the diaper in an unfolded state (front-back direction length from an edge of a waist opening WO of the front body F to an edge of a waist opening WO of the back body B), and a reference character X represents the maximum width of the diaper in an unfolded state.

The underpants-type disposable diaper in the present form has a lower torso region T defined as a front-back direction range (front-back direction range from the waist opening WO to an upper end of the leg opening LO) having the side seal portion 12A, and an intermediate region L defined as a front-back direction range of a portion forming the leg opening LO (between a front-back direction region having the side seal portion 12A of the front body F and a front-back direction region having the side seal portion 12A of the back body B). The lower torso region T can be divided into a "waist portion" W conceptually forming an edge of the waist opening and an "under-waist portion" U which is a portion lower than the waist portion W. Usually, in a case where the lower torso region T has a boundary in which a stretching stress in a width direction WD changes (for example, the fineness of an elastic member or the stretch rate thereof changes), a portion closer to the waist opening WO than the boundary closest to the waist opening WO is the waist portion W. In a case where there is no such a boundary, a portion closer to the waist opening WO than the absorber 56 or the inner member 200 is the waist portion W. The front-back direction length varies depending on the size of a product and can be appropriately determined. For example, the length of the waist portion W can be 15 to 40 mm, and the length of the under-waist portion U can be 65 to 120 mm. Meanwhile, both side edges of the intermediate region L are each narrowed in a substantially U shape or a curved shape so as to follow a periphery of a wearer's leg, and these side edges are portions along the periphery of a wearer's leg.

(Outer Member)

The outer members 12F and 12B are not formed as an integral outer member passing a crotch from the front body F to the back body B, but are formed of the front outer member 12F forming at least a lower torso portion of the front body F and the back outer member 12B forming at least a lower torso portion of the back body B. The front outer member 12F and the back outer member 12B are not continuous on a crotch side, and are separated from each other in the front-back direction LD. A separation distance thereof 12d can be about 150 to 250 mm, for example.

The outer members 12F and 12B each have a lower torso portion which is a front-back direction range corresponding to the lower torso region T. In the present form, the front-back direction size of the back outer member 12B is longer than that of the front outer member 12F, and the front outer member 12F does not have a portion corresponding to the intermediate region L, but the back outer member 12B has a gluteal cover portion C extending from the lower torso region T toward the intermediate region L. Although not illustrated, also in the front outer member 12F, an inguinal cover portion extending from the lower torso region T toward the intermediate region L may be disposed, or the inguinal cover portion may be disposed without a gluteal cover portion. Alternatively, in both the front outer member 12F and the back outer member 12B, it is not necessary to dispose a portion corresponding to the intermediate region L. In the illustrated embodiment, a lower edge of the gluteal cover portion C is formed linearly in the width direction WD like a lower edge of the front outer member 12F, but may be a curve so as to be closer to the waist opening as the lower edge of the gluteal cover portion C goes outward in the width direction.

The front-back direction size of a side edge of the gluteal cover portion C only needs to be determined appropriately. However, when the size is too long, a corner of the side edge on the leg opening LO side may flatter, and an appearance and wearing feeling may be deteriorated. Therefore, the size is preferably 20 mm or less.

As illustrated in FIGS. 4 and 5, the outer members 12F and 12B are formed by bonding an outer sheet layer 12S and an inner sheet layer 12H located on an outer side and an inner side of elastic members 15 to 19 described later, respectively, by a bonding means such as a hot melt adhesive or welding. A sheet material forming the outer sheet layer 12S and a sheet material forming the inner sheet layer 12H may be formed of a common single sheet material or may be formed of individual sheet materials. That is, in the former case, the inner sheet layer 12H and the outer sheet layer 12S are formed by an inner portion and an outer portion of a single sheet of a sheet material folded back at an edge of the waist opening WO (which may be an edge on a leg opening side) in a part or the whole of the outer member, respectively. Incidentally, in the former form, the number of materials of the sheet material is small advantageously, and in the latter form, positional deviation is unlikely to occur when the inner sheet layer 12H and the outer sheet layer 12S are bonded to each other. The illustrated embodiment corresponds to the latter, and the sheet material forming the inner sheet layer 12H extends only to an edge of the waist opening WO. However, the sheet material forming the outer sheet layer 12S goes around a waist side edge of the sheet material of the inner sheet layer 12H and folded back inward. A folded-back portion 12r extends so as to cover an end portion of the inner member 200 on the waist opening side.

The sheet material used for the outer sheet layer 12S and the inner sheet layer 12H is not particularly limited, but is preferably a nonwoven fabric. Examples thereof include a nonwoven fabric formed of a synthetic fiber such as an olefin-based fiber including polyethylene and polypropylene, a polyester-based fiber, or a polyamide-based fiber, or a mixed fiber or a composite fiber using two or more kinds of these fibers. Furthermore, the nonwoven fabric may be manufactured by any processing. Examples of a processing method include known methods such as a spunlacing method, a spunbonding method, a thermal bond method, a melt blown method, a needle punching method, an air through method, and a point bond method. In a case where a nonwoven fabric is used, the nonwoven fabric preferably has a basis weight of about 10 to 30 g/m$^2$.

(Stretchable Region/Non-Stretchable Region)

In each of the outer members 12F and 12B, in order to enhance fitting of a wearer to a lower torso, the elastic members 15 to 19 are disposed between the outer sheet layer 12S and the inner sheet layer 12H, and a stretchable region A2 that elastically stretches and contracts in the width direction WD along with stretching and contracting of the elastic members is formed. In the stretchable region A2, in a natural length state, the outer sheet layer 12S and the inner sheet layer 12H contract along with contraction of an elastic member to form wrinkles or pleats. When the elastic member stretches in a longitudinal direction, it is possible to stretch the outer sheet layer 12S and the inner sheet layer 12H to a predetermined stretch rate at which the outer sheet layer 12S and the inner sheet layer 12H stretch without wrinkles. As the elastic members 15 to 19, in addition to an elongated elastic member (illustrated example) such as a rubber thread, a known elastic member such as a belt-shaped member, a net-shaped member, or a film-shaped member can be used without particular limitation. As the elastic members 15 to 19, either a synthetic rubber or a natural rubber may be used.

For bonding the outer sheet layer 12S and the inner sheet layer 12H in the outer members 12F and 12B and fixing the elastic members 15 to 19 sandwiched therebetween, at least one of a hot melt adhesive by various application methods and a fixing means by material welding such as heat sealing or ultrasonic sealing can be used. When the entire surfaces of the outer members 12F and 12B are fixed rigidly, softness is impaired. Therefore, preferably, a portion other than a bonded portion of the elastic members 15 to 19 is not bonded or weakly bonded. In the illustrated embodiment, by applying a hot melt adhesive only to an outer peripheral surface of the elastic members 15 to 19 by an application means such as a comb gun or a SureWrap nozzle, and sandwiching the elastic members 15 to 19 between both the sheet layers 12S and 12H, the elastic members 15 to 19 are fixed to both the sheet layers 12S and 12H only with the hot melt adhesive applied to the outer peripheral surfaces of the elastic members 15 to 19, and both the sheet layers 12S and 12H are fixed to each other. The elastic members 15 to 19 can be fixed to the outer sheet layer 12S and the inner sheet layer 12H only at both end portions in a stretchable direction in a stretchable region.

The elastic members 15 to 19 in the illustrated embodiment will be described in more detail. Between the outer sheet layer 12S and the inner sheet layer 12H in the waist portion W of the outer members 12F and 12B, a plurality of waist portion elastic members 17 is attached at intervals in a front-back direction so as to be continuous over the entire width direction WD. One or more waist portion elastic members 17 disposed in a region adjacent to the under-waist portion U may overlap with the inner member 200, or may be disposed on both sides thereof in the width direction except for the center in the width direction overlapping with the inner member 200. As the waist portion elastic member 17, it is preferable to dispose 3 to 22 rubber threads each having a fineness of 155 to 1880 dtex, particularly about 470 to 1240 dtex (in a case of a synthetic rubber, having a cross section of 0.05 to 1.5 mm$^2$, particularly about 0.1 to 1.0 mm$^2$ in a case of a natural rubber) at intervals of 4 to 12 mm. A resultant stretch rate of the waist portion W in the width direction WD is preferably 150 to 400%, and particularly preferably about 220 to 320%. In the waist portion W, all of the waist portion elastic members 17 in the front-back direction LD do not have to have the same fineness and the same stretch rate. For example, the fineness and the stretch rate of the elastic member 17 may be different between an upper portion and a lower portion of the waist portion W.

Between the outer sheet layer 12S and the inner sheet layer 12H in the under-waist portion U of the outer members 12F and 12B, a plurality of under-waist portion elastic members 15 and 19 formed of an elongated elastic member is disposed at intervals in a front-back direction.

As the under-waist portion elastic members 15 and 19, it is preferable to dispose 5 to 30 rubber threads each having a fineness of 155 to 1880 dtex, particularly about 470 to 1240 dtex (in a case of a synthetic rubber, having a cross section of 0.05 to 1.5 mm$^2$, particularly about 0.1 to 1.0 mm$^2$ in a case of a natural rubber) at intervals of 1 to 15 mm, particularly 3 to 8 mm. A resultant stretch rate of the under-waist portion U in the width direction WD is preferably 200 to 350%, and particularly preferably about 240 to 300%.

Between the outer sheet layer 12S and the inner sheet layer 12H in the gluteal cover portion C of the back outer member 12B, a cover portion elastic member 16 formed of an elongated elastic member is attached.

As the cover portion elastic member 16, it is preferable to dispose one or a plurality of rubber threads, at intervals in the front-back direction, having a fineness of 155 to 1880 dtex, particularly about 470 to 1240 dtex (in a case of a synthetic rubber, having a cross section of 0.05 to 1.5 mm$^2$, particularly about 0.1 to 1.0 mm$^2$ in a case of a natural rubber). A resultant stretch rate of the gluteal cover portion C in the width direction WD is preferably 150 to 300%, and particularly preferably about 180 to 260%.

In a case where an inguinal cover portion is disposed in the front outer member 12F, the cover portion elastic member can be disposed similarly.

In a case where the elastic members 15, 16, and 19 are disposed in a front-back direction range having the absorber 56 like the under-waist portion U and the gluteal cover portion C in the illustrated embodiment, in order to prevent contraction of the absorber 56 in the width direction WD in a part or the whole thereof, a width direction intermediate portion including a part or the whole of a portion overlapping with the absorber 56 in the width direction WD (preferably including the whole of the inner and outer bonded portions 201 and 202) is a non-stretchable region A1, and both sides thereof in the width direction are stretchable regions A2. The waist portion W is preferably the stretchable region A2 over the entire width direction WD. However, like the under-waist portion U, the waist portion W may have the non-stretchable region A1 in a width direction intermediate portion.

The stretchable region A2 and the non-stretchable region A1 can be formed by supplying elastic members 15 to 17 and 19 between the inner sheet layer 12H and the outer sheet layer 12S, fixing the elastic members 15, 16, and 19 in at least both end portions in a stretchable direction in the stretchable region A2 through a hot melt adhesive without fixing the elastic members 15, 16, and 19 in a region to be the non-stretchable region A1, and cutting the elastic members 15, 16, and 19 at one place in a width direction intermediate portion or cutting almost the whole of the elastic members 15, 16, and 19 finely by means of pressing and heating of the elastic members 15, 16, and 19 in the region to be the non-stretchable region A1 to leave elasticity in the stretchable region A2 and destroy elasticity in the non-stretchable region A1. In the former case, as illustrated in FIG. 4, in the non-stretchable region A1, a cutting residue continuous from the elastic members 15, 16, and 19 in the stretchable region A2 remains between the outer sheet layer 12S and the inner sheet layer 12H while being contracted to a natural length alone as an unnecessary elastic member 18. In the latter case, although not illustrated, a cutting residue continuous from the elastic members 15, 16, and 19 in the stretchable region A2 and a cut piece of an elastic member not continuous from the elastic members 15, 16, and 19 in either of the stretchable regions A2 remain between the outer sheet layer 12S and the inner sheet layer 12H while being contracted to a natural length alone as an unnecessary elastic member.

(Cover Nonwoven Fabric)

In an outer member separated type underpants-type disposable diaper, the inner member 200 is exposed between the front outer member 12F and the back outer member 12B. Therefore, in order to prevent the liquid impervious sheet 11 from being exposed to a back surface of the inner member 200, the outer member separated type underpants-type disposable diaper preferably includes a cover nonwoven fabric 13 covering the back surface of the inner member 200 from a portion between the front outer member 12F and the inner member 200 to a portion between the back outer member 12B and the inner member 200.

As a nonwoven fabric used for the cover nonwoven fabric 13, for example, a material similar to those of the outer members 12F and 12B can be appropriately selected, and the nonwoven fabric used for the cover nonwoven fabric 13 is not particularly limited by the type of a fiber or a method for bonding (interlacing) fibers. However, it is desirable to use an air through nonwoven fabric. In this case, the basis weight is preferably 20 to 40 g/m$^2$ and the thickness is preferably 0.3 to 1.0 mm. As the cover nonwoven fabric 13, an imperforated nonwoven fabric having no hole passing therethrough from the front to the back or a perforated nonwoven fabric having many holes passing therethrough from the front to the back at intervals may be used.

The front-back direction range of the cover nonwoven fabric 13 is not particularly limited, and as illustrated in FIG. 5, may extend in the front-back direction LD over the entire region from a front end to a back end of the inner member 200. As illustrated in FIG. 7, the front-back direction range of the cover nonwoven fabric 13 may extend in the front-back direction LD from a front-back direction intermediate position of a region where the front outer member 12F and the inner member 200 overlap with each other to a front-back direction intermediate position of a region where the back outer member 12B and the inner member 200 overlap with each other. In the case of the example illustrated in FIG. 7, a front-back direction length 13y of an overlapping portion between the cover nonwoven fabric 13 and the front outer member 12F and a front-back direction length 13y of an overlapping portion between the cover nonwoven fabric 13 and the back outer member 12B can be appropriately determined, but can be each about 20 to 40 mm in a usual case.

The width direction range of the cover nonwoven fabric 13 is a range in which a back surface exposed portion of the liquid impervious sheet 11 can be concealed. For this reason, in the illustrated example, the liquid impervious sheet 11 is exposed between base ends of the left and right rising gathers 60. Therefore, the cover nonwoven fabric 13 is disposed so as to cover a width direction range from a back surface side of a base portion of at least one of the rising gathers 60 to a back surface side of a base portion of the other of the rising gathers 60. This makes it possible to conceal the liquid impervious sheet 11 with the cover nonwoven fabric 13 and a gather sheet 62 of the rising gather 60. In addition, not by covering a back surface side of the base portion of the rising gather 60 with width direction both end portions of the cover nonwoven fabric 13 but by covering a back surface side of the width direction both end portions of the cover nonwoven fabric 13 with the gather sheet 62, it is possible to conceal the liquid impervious sheet 11 with the cover nonwoven fabric 13 and the gather sheet 62.

The inner surface and the outer surface of the cover nonwoven fabric 13 can be bonded to facing surfaces thereof via a hot melt adhesive. A fixing region of the cover nonwoven fabric 13 can extend to the entire front-back direction and the entire width direction of the cover nonwoven fabric 13, or a part thereof can be non-fixed. For example, when width direction both end portions of the cover nonwoven fabric 13 are non-fixed, even if a side of the absorber 56 is contracted somewhat due to an influence of the rising gather 60, the influence is small, and wrinkles or creases are less likely to be formed in the cover nonwoven fabric 13 advantageously. In this case, the widths of the non-fixed portions at width direction both end portions of the cover nonwoven fabric 13 may be determined appropriately, but can be, for example, 3 to 10 mm, preferably 5 to 8 mm.

(Inner and Outer Bonded Portion)

The inner member 200 can be fixed to the outer members 12F and 12B by a bonding means by material welding such as heat sealing or ultrasonic sealing, or with a hot melt adhesive. In the illustrated example, via a hot melt adhesive applied to the back surface of the inner member 200, that is, the back surface of the liquid impervious sheet 11 and a root portion 65 of the rising gather 60 in this case, the inner member 200 is fixed to the inner surfaces of the outer members 12F and 12B. The inner and outer bonded portions 201 and 202 for fixing the inner member 200 to the outer members 12F and 12B can be disposed in almost the entire region where the inner member 200 overlaps with the outer members 12F and 12B as illustrated in FIG. 2, and can be disposed, for example, in a portion excluding width direction both end portions of the inner member 200.

(Inner Member)

The inner member 200 can adopt an arbitrary shape, but is rectangular in the illustrated form. As illustrated in FIGS. 1 to 5, the inner member 200 includes an absorbent element 50, a top sheet 30 covering a front surface side (body side) of the absorbent element 50, and the liquid impervious sheet 11 covering a back surface side of the absorbent element 50, and is a portion for performing an absorption holding function. A reference numeral 40 represents an intermediate sheet (second sheet) disposed between the top sheet 30 and the absorbent element 50 in order to rapidly transfer a liquid that has passed through the top sheet 30 to the absorbent element 50. A reference numeral 60 represents a rising gather 60 extending so as to come into contact with a periphery of a wearer's leg from both sides of the inner member 200 in order to prevent leakage of excrement into both sides of the inner member 200.

(Absorbent Element)

The absorbent element 50 includes the absorber 56 and the wrapping sheet 58 wrapping the entire absorber 56. The wrapping sheet 58 can also be omitted.

(Absorber)

The absorber 56 can be formed by an assembly of fibers. As this fiber assembly, in addition to those obtained by accumulating short fibers such as fluff pulps or synthetic fibers, a filament assembly obtained by opening a tow (fiber bundle) of synthetic fibers such as cellulose acetate as necessary can also be used. In a case where fluff pulps or short fibers are accumulated, a fiber basis weight may be, for example, about 100 to 300 $g/m^2$. In a case of a filament assembly, a fiber basis weight may be, for example, about 30 to 120 $g/m^2$. In a case of a synthetic fiber, a fineness is, for example, 1 to 16 dtex, preferably 1 to 10 dtex, and more preferably 1 to 5 dtex. In a case of a filament assembly, the filament may be formed of non-crimped fibers but is preferably formed of crimped fibers. The degree of crimp of the crimped fibers may be, for example, about 5 to 75, preferably 10 to 50, and more preferably 15 to 50 per 2.54 cm. In addition, a uniformly crimped fiber can be used. In the absorber 56, super absorbent polymer particles are preferably dispersed and held.

The absorber 56 may have a rectangular shape. However, as illustrated in FIG. 7 and the like, the absorber 56 preferably has an hourglass shape having a narrower portion 56N with a narrower width than front-back direction both sides thereof in a front-back direction intermediate portion because fitting of the absorber 56 itself and the rising gather 60 to a periphery of a leg is improved.

The size of the absorber 56 can be determined appropriately as long as the absorber 56 includes a crotch portion. However, the absorber 56 preferably extends to peripheral edges of the inner member 200 or the vicinity thereof in the front-back direction LD and the width direction WD. Note that a reference numeral 56X represents the maximum width of the absorber 56.

(Super Absorbent Polymer Particles)

The absorber 56 may contain super absorbent polymer particles partially or entirely. The super absorbent polymer particles include "powder" in addition to "particles". As super absorbent polymer particles 54, those used for this type of disposable diaper can be used as they are. For example, when sieving using a standard sieve of 500 μm (JIS Z8801-1: 2006) (shake for five minutes) is performed, particles in which a ratio of particles remaining on the sieve is 30% by weight or less are desirable. When sieving using a standard sieve of 180 μm (JIS Z8801-1: 2006) (shake for five minutes) is performed, particles in which a ratio of particles remaining on the sieve is 60% by weight or more are desirable.

A material of the super absorbent polymer particles can be used without particular limitation, but those having a water absorption capacity of 40 g/g or more are preferable. Examples of the super absorbent polymer particles include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the super absorbent polymer particles, a usually used particulate material shape is suitable, but other shapes can also be used.

As the super absorbent polymer particles, those having a water absorption rate of 70 seconds or less, particularly 40 seconds or less are suitably used. When the water absorption rate is too slow, so-called returning that a liquid supplied into the absorber 56 returns out of the absorber 56 tends to occur.

As the super absorbent polymer particles, those having a gel strength of 1000 Pa or more are suitably used. This makes it possible to effectively suppress sticky feeling after liquid absorption even in a case of using the bulky absorber 56.

The basis weight of the super absorbent polymer particles can be appropriately determined depending on the absorption amount required for an application of the absorber 56. Therefore, the basis weight can be 50 to 350 g/m$^2$ although this cannot be applied generally. The basis weight of a polymer of less than 50 g/m$^2$ makes it difficult to secure the absorption amount. The basis weight of more than 350 g/m$^2$ saturates an effect.

The content of the super absorbent polymer particles in a planar direction of the absorber 56 can be adjusted if necessary. For example, the content at a liquid excretion site can be larger than that at another site. It is also possible to locally dispose a portion where no super absorbent polymer particle is present (for example, in a spot shape) in a planar direction of the absorber 56.

(Wrapping Sheet)

In a case where the wrapping sheet 58 is used, as a material thereof, tissue paper, particularly, crepe paper, a nonwoven fabric, a polylaminated nonwoven fabric, a sheet with small holes, and the like can be used. However, it is desirable that the wrapping sheet 58 is a sheet from which super absorbent polymer particles do not escape. In a case where a nonwoven fabric is used instead of crepe paper, a hydrophilic SMS nonwoven fabric (SMS, SSMMS, or the like) is particularly suitable, and polypropylene, a polyethylene/polypropylene composite material, or the like can be used as a material thereof. A nonwoven fabric having a basis weight of 5 to 40 g/m$^2$, particularly of 10 to 30 g/m$^2$ is desirable.

A wrapping mode of the wrapping sheet 58 can be determined appropriately. However, a form is preferable in which the wrapping sheet 58 is wound around the absorber 56 cylindrically so as to surround front and back surfaces and both side surfaces of the absorber 56, the front and back end portions of the wrapping sheet 58 are caused to protrude from the front and back of the absorber 56, and a wound and overlapping portion and an overlapping portion of the front and back protruding portions are bonded with a hot melt adhesive or by a bonding means such as material welding from viewpoints of ease of manufacture, prevention of leakage of the super absorbent polymer particles from front and back edges, and the like.

(Top Sheet)

The top sheet 30 transmits a liquid, and examples thereof include a perforated or imperforated nonwoven fabric and a porous plastic sheet. Among these materials, the nonwoven fabric is not particularly limited concerning a raw material fiber thereof. Examples thereof include a synthetic fiber such as an olefin-based fiber including polyethylene and polypropylene, a polyester-based fiber, or a polyamide-based fiber, a regenerated fiber such as rayon or cupra, a natural fiber such as cotton, and a mixed fiber and a composite fiber in which two or more kinds of these fibers are used. Furthermore, the nonwoven fabric may be manufactured by any processing. Examples of a processing method include known methods such as a spunlacing method, a spunbonding method, a thermal bond method, a melt blown method, a needle punching method, an air through method, and a point bond method. For example, if softness and drapeability are demanded, a spunbonding method and a spunlacing method are preferable processing methods. If bulkiness and softness are demanded, an air through method, a point bond method, and a thermal bond method are preferable processing methods.

The top sheet 30 may be formed of a single sheet or a laminated sheet obtained by bonding two or more sheets to each other. Similarly, the top sheet 30 may be formed of a single sheet or two or more sheets in a plane direction.

Both sides of the top sheet 30 may be folded back to a back surface side at a side edge of the absorbent element 50 or may protrude from the side edge of the absorbent element 50 to a lateral side without being folded back.

For the purpose of preventing positional deviation with respect to a back surface side member or the like, it is desirable that the top sheet 30 is fixed to a member adjacent to the back surface side by a bonding means by material welding such as heat sealing or ultrasonic sealing, or with a hot melt adhesive. In the illustrated example, the top sheet 30 is fixed to a surface of an intermediate sheet 40 and a surface of a portion located on a front surface side of the absorber 56 in a wrapping sheet 58 with a hot melt adhesive applied to a back surface thereof.

(Intermediate Sheet)

In order to quickly transfer a liquid that has passed through the top sheet 30 to the absorber, it is possible to dispose the intermediate sheet (also referred to as "second sheet") 40 having a higher liquid transmission rate than the top sheet 30. The intermediate sheet 40 is used in order to rapidly transfer a liquid to the absorber to enhance absorption performance of the absorber, and to prevent a "returning" phenomenon of the absorbed liquid from the absorber. The intermediate sheet 40 can be omitted.

Examples of the intermediate sheet 40 include a similar material to that of the top sheet 30, a spunlaced nonwoven fabric, a spunbonded nonwoven fabric, an SMS nonwoven fabric, a pulp nonwoven fabric, a mixed sheet of pulp and rayon, a point bonded nonwoven fabric, and crepe paper. In particular, an air through nonwoven fabric is preferable because of being bulky. As the air through nonwoven fabric, a composite fiber having a core-sheath structure is preferably used. In this case, a resin used for the core may be polypropylene (PP) but is preferably polyester (PET) having high rigidity. The basis weight is preferably 17 to 80 g/m$^2$, and more preferably 25 to 60 g/m$^2$. A raw material fiber of the nonwoven fabric preferably has a fineness of 2.0 to 10 dtex. In order to make the nonwoven fabric bulky, as mixed fibers of all or some of raw material fibers, eccentric fibers having no core in the center, hollow fibers, eccentric and hollow fibers are also preferably used.

The intermediate sheet 40 in the illustrated example is disposed at the center so as to be shorter than the width of the absorber 56, but may be disposed over the maximum width. The front-back direction length of the intermediate sheet 40 may be the same as the maximum length of the diaper, may be the same as the length of the absorbent element 50, or may be within a short length range centered on a liquid receiving region.

For the purpose of preventing positional deviation with respect to a back surface side member or the like, it is desirable that the intermediate sheet 40 is fixed to a member adjacent to the back surface side by a bonding means by material welding such as heat sealing or ultrasonic sealing, or with a hot melt adhesive. In the illustrated example, the intermediate sheet 40 is fixed to a surface of a portion located on a front surface side of the absorber 56 in the wrapping sheet 58 with a hot melt adhesive applied to a back surface thereof.

(Liquid Impervious Sheet)

A material of the liquid impervious sheet 11 is not particularly limited, but examples thereof include a plastic film formed of an olefin-based resin such as polyethylene or polypropylene, a laminated nonwoven fabric having a plastic film disposed on a surface of a nonwoven fabric, and a laminated sheet obtained by superposing and bonding a nonwoven fabric or the like to a plastic film. For the liquid impervious sheet 11, it is preferable to use a liquid impervious and moisture pervious material favorably used from a viewpoint of preventing stuffiness. As a moisture pervious plastic film, a microporous plastic film obtained by kneading an inorganic filler in an olefin-based resin such as polyethylene or polypropylene, molding a sheet, and then stretching the sheet in a monoaxial or biaxial direction is widely used. In addition, a nonwoven fabric using a micro denier fiber, a nonwoven fabric that has reinforced leakproofness by reducing a space between fibers by applying heat and pressure, and a sheet that has become liquid impervious without using a plastic film by a method for applying a super absorbent polymer, a hydrophobic resin, or a water repellent agent can be used as the liquid impervious sheet 11. However, it is desirable to use a resin film in order to obtain sufficient bonding strength at the time of bonding to a cover nonwoven fabric 13 described later through a hot melt adhesive.

The liquid impervious sheet 11 may have a width housed in a back surface side of the absorbent element 50 as illustrated in the drawing, or may go around both sides of the absorbent element 50 and extend to both sides of a side surface of the top sheet 30 of the absorbent element 50 in order to enhance leakproofness. The extending portion appropriately has a width of about 5 to 20 mm on each of the left and the right.

(Rising Gather)

The rising gather 60 has a rising portion 68 rising from a side of the inner member 200, and the rising portion 68 comes into contact with a region from a wearer's inguinal portion to the wearer's gluteal region through a periphery of the wearer's leg to prevent side leakage.

The rising gather in the illustrated example is formed by folding back the belt-shaped gather sheet 62 having a length equal to the front-back direction length of the inner member 200 in the width direction WD at a tip portion to be folded in two to obtain a two-layer structure, and fixing a plurality of elongated gather elastic members 63 between the layers in a stretched state in a longitudinal direction at intervals in the width direction WD. A base portion of the rising gather 60 opposite to a tip portion thereof (an end portion opposite to the sheet-folded portion in the width direction WD) is the root portion 65 fixed to a side of a back surface side of the liquid impervious sheet 11 in the inner member 200, and a portion other than the root portion 65 is a main unit portion 66 extending from the root portion 65. The main unit portion 66 has a first portion 60A extending from both sides of a surface of the inner member 200 toward the center in the width direction, and a second portion 60B folded back at a tip of the first portion 60A and extending outward in the width direction. A front end portion FEP and a back end portion BEP of the main unit portion 66 are a front fallen portion 67F and a back fallen portion 67B fixed to a side surface of the top sheet 30 in a state of falling down, respectively. Meanwhile, a front-back direction intermediate portion located between the front fallen portion 67F and the back fallen portion 67B is the non-fixed rising portion 68, and the gather elastic member 63 extending in the front-back direction LD is fixed in a stretched state to at least a tip portion of the rising portion 68.

Characteristically, the front fallen portion 67F and the back fallen portion 67B each have a protruding portion 69 where the second portion 60B protrudes 5 to 40 mm outward in the width direction than a side edge of the first portion 60A. The protruding portion 69 of the front fallen portion 67F has a protruding fixing portion CF fixed to the front outer member 12F overlapping with a back surface side of the protruding portion 69, and the protruding portion 69 of the back fallen portion 67B has a protruding fixing portion CF fixed to the back outer member 12B overlapping with a back surface side of the protruding portion 69.

In the rising gather 60 configured as described above, in a wearing state, as illustrated by a two-dot chain line in FIG. 3, the rising portion 68 rises so as to come into contact with a body surface of a wearer by a contraction force of the gather elastic member 63. More specifically, in the rising gather 60 in the illustrated example, as illustrated by a two-dot chain line in FIG. 3, the width of the inner member 200 is narrowed by rise of the rising portion 68 of the rising gather 60 at an intermediate portion of the inner member 200 in a front-back direction LD. However, as illustrated in FIG. 4, by disposing the protruding portions 69 fixed to the front outer member 12F and the back outer member 12B in the second portions 60B of the front fallen portion 67F and the back fallen portion 67B, respectively, the width of the inner member 200 is increased as the inner member 200 goes toward both sides in the front-back direction. For this reason, despite of the outer member separated type disposable diaper, a covering property of the vicinity of a corner portion formed by an edge on the leg opening side of each of the front outer member 12F and the back outer member 12B and a side edge of the inner member 200, that is, a covering property of a gluteal region and an inguinal portion is improved.

As illustrated in FIGS. 8 to 11, the front fallen portion 67F and the back fallen portion 67B each have a first fixing portion AF where the first portion 60A is bonded to the top sheet 30 and the second fixing portion BF where the second portion 60B is bonded to the first portion 60A in order to set a state of falling down. For bonding facing surfaces in the first fixing portion AF and the second fixing portion BF, at least one of a hot melt adhesive by various application methods and a means by material welding such as heat sealing or ultrasonic sealing can be used. In this case, bonding in the first fixing portion AF and bonding in the second fixing portion BF may be performed by the same means or by different means. Note that the drawings illustrate a case where bonding is performed with a hot melt adhesive in both the first fixing portion AF and the second fixing portion BF. Bonding of facing surfaces in the protruding fixing portion CF can be performed similarly to bonding of facing surfaces in the first fixing portion AF and the second fixing portion BF.

As illustrated in FIGS. 8 and 9, preferably, the back fallen portion 67B has a full fallen region H1 having the first fixing portion AF and the second fixing portion BF on a back side, and has a half fallen region H2 not having the first fixing portion AF and having the second fixing portion BF on a front side, and a front-back direction size Z2 of the second fixing portion BF is twice or more a front-back direction size Z1 of the first fixing portion AF. As described above, by disposing the half fallen region having only the second fixing portion BF on the front side of the back fallen portion 67B, the second portion 60B does not easily fall inward in the width direction. Therefore, an upper surface fits well to a surface of a gluteal region, and hardly bites into an intergluteal cleft. In addition, the half fallen region of the back fallen portion 67B comes into contact with a bulging portion of the buttock. Therefore, even if the second portion 60B is bonded to the first portion 60A, there is no risk that a gap may be generated between the diaper and a body.

As illustrated in FIGS. 10 and 11, when the front fallen portion 67F has the full fallen region H1 having the first fixing portion AF and the second fixing portion BF on a front side, and has the half fallen region H2 not having the second fixing portion BF and having the first fixing portion AF on a back side, the second portion 60B firmly rises on the basis of the first portion 60A fixed by the first fixing portion AF, and the diaper fits to a depression of an inguinal portion in a more stable posture. Therefore, this is preferable.

As described above, when the rising gather 60 has the protruding portion 69, a problem that the rising portion 68 falls inward hardly occurs. Therefore, the range of the rising portion 68 is preferably widened in the front-back direction LD to increase fitting to a gluteal region and an inguinal portion. Specifically, preferably, the back fallen portion 67B is disposed on a front edge of the back outer member 12B or on a back side thereof, and the front fallen portion 67F is disposed on a back edge of the front outer member 12F or on a front side thereof.

A front-back direction size Z3 of the protruding fixing portion CF can be determined appropriately. When the front-back direction size Z3 of the protruding fixing portion CF in the back fallen portion 67B is 0.7 to 1 time the size of a longer one out of the front-back direction size Z1 of the first fixing portion AF and the front-back direction size Z2 of the second fixing portion BF located on a lateral side thereof, a covering property of a gluteal region is improved without depending on whether the front-back direction size Z1 of the first fixing portion AF is larger or smaller than the front-back direction size Z2 of the second fixing portion BF. Therefore, this is preferable. For example, in the back fallen portion 67B, as illustrated in FIG. 12, even when the half fallen region H2 does not have the second fixing portion BF, if the front-back direction size Z3 of the protruding fixing portion CF is sufficiently long, the fixed length of the second portion 60B is long as a whole. Therefore, even in this case, the second portion 60B does not easily fall inward in the width direction. Therefore, an upper surface fits well to a surface of a gluteal region, and hardly bites into an intergluteal cleft. Meanwhile, when the front-back direction size Z3 of the protruding fixing portion CF in the front fallen portion 67F is 0.7 to 1 time the size of a shorter one out of the front-back direction size Z1 of the first fixing portion AF and the front-back direction size Z2 of the second fixing portion BF located on a lateral side thereof, the diaper fits to a depression of an inguinal portion in a more stable posture. Therefore, this is preferable.

As described above, the front outer member 12F and the back outer member 12B of the underpants-type disposable diaper generally each have a stretchable region A2 that stretches and contracts in the width direction. Therefore, as illustrated in FIGS. 2 and 4, preferably, the stretchable region A2 in each of the front outer member 12F and the back outer member 12B is disposed so as to include a portion overlapping with the protruding portion 69, and the protruding fixing portion CF is fixed to the stretchable region A2 to make the protruding fixing portion CF stretchable together with the stretchable region A2. As a result, before wearing, the protruding portion 69 contracts together with the front outer member 12F and the back outer member 12B, and the leg opening becomes wider. Therefore, a hand or a foot easily passes through the leg opening during wearing work. Then, at the time of wearing, the protruding portions 69 stretches and extends together with the front outer member 12F and the back outer member 12B, and a gluteal region and an inguinal portion are covered.

When the protruding fixing portion CF is stretchable in the width direction together with the front outer member 12F and the back outer member 12B, if the protruding fixing portion CF is stretchable in the front-back direction LD by the gather elastic member 63, the protruding portion 69 contracts in the width direction and the front-back direction LD and becomes like a hard bump in a wearing state. Therefore, a wearing feeling may be deteriorated. Therefore, it is desirable that the protruding fixing portion CF does not contract by contraction of the gather elastic member 63. That is, it is preferable to dispose the plurality of gather elastic members 63 in the second portion 60B of the rising portion 68 at intervals not only at a tip portion 61 but also at an end portion on the first portion 60A side. However, preferably, among the gather elastic members 63, a gather elastic member 63 having the protruding fixing portion CF in the front-back direction LD does not extend to the protruding fixing portion CF, or even if extending to the protruding fixing portion CF, is not fixed to the gather sheet 62 to prevent a contraction force from acting.

Meanwhile, it is practically difficult to fix even a side edge portion of the protruding portion 69 to the front outer member 12F and the back outer member 12B. Therefore, as in the illustrated example, the side edge portion of the protruding portion 69 is preferably a non-fixed free edge 69f. In this case, as illustrated in FIGS. 8 to 11, when the gather elastic member 63 disposed at a tip portion 61 of the rising portion 68 is extended to the free edge 69f of the protruding portion 69, and the free edge 69f rises by contraction of the gather elastic member 63, leakage prevention is enhanced. Therefore, this is preferable.

A material of the gather sheet 62 is not particularly limited. However, a product obtained by subjecting a soft nonwoven fabric having excellent uniformity and concealability, such as a spunbonded nonwoven fabric (SS, SSS, or the like), an SMS nonwoven fabric (SMS, SSMMS, or the like), or a melt blown nonwoven fabric, to a water repellent treatment with silicon or the like as necessary can be used suitably. The nonwoven fabric preferably has a fiber basis weight of about 10 to 30 g/m$^2$. As the gather elastic member 63, a rubber thread or the like can be used. When a spandex rubber thread is used, the spandex rubber thread preferably has a fineness of 470 to 1240 dtex, preferably 620 to 940 dtex. The rubber thread preferably has a stretch rate of 150 to 350%, preferably 200 to 300% at the time of fixing. Note that the term "stretch rate" means a value obtained when a natural length is assumed to be 100%. As illustrated in the drawing, a waterproof film 64 can be interposed between the two portions obtained by folding the gather sheet 62, and in this case, the gather sheet 62 can be partially omitted in a portion where the waterproof film 64 is present. However, in order to impart a cloth-like appearance and a cloth-like texture to a product, at least an outer surface from a base end to a tip of the rising gather 60 needs to be formed of the gather sheet 62 as in the illustrated embodiment.

The number of the gather elastic members 63 is preferably 2 to 6, and more preferably 3 to 5. A disposition interval 60d is suitably 3 to 10 mm. With such a configuration, a range where the gather elastic member 63 is disposed easily comes into contact with a skin with a surface. The gather elastic member 63 may be disposed not only on a tip side but also on a root side. It is desirable that a contraction force of the gather elastic member 63 does not act on the first fixing portion AF, the second fixing portion BF, and the protruding fixing portion CF in the front fallen portion 67F and the back fallen portion 67B. Note that the portion on which a contraction force of the gather elastic member 63 does not act includes, in addition to a portion not including the gather elastic member 63, the gather elastic member 63 not fixed to the gather sheet 62 and contracted to a natural length.

In the rising portion 68, for bonding an inner layer and an outer layer of the gather sheet 62 to each other or fixing the gather elastic member 63 sandwiched therebetween, at least one of a hot melt adhesive by various application methods and a fixing means by material welding such as heat sealing or ultrasonic sealing can be used. When the entire surfaces of the inner layer and the outer layer of the gather sheet 62 are bonded to each other, softness is impaired. Therefore, preferably, a portion other than a bonded portion of the gather elastic member 63 is not bonded or weakly bonded. In the illustrated embodiment, by applying a hot melt adhesive only to an outer peripheral surface of the gather elastic member 63 by an application means such as a comb gun or a SureWrap nozzle, and sandwiching the gather elastic member 63 between the inner layer and the outer layer of the gather sheet 62, the gather elastic member 63 is fixed to the inner layer and the outer layer of the gather sheet 62, and the inner layer and the outer layer of the gather sheet 62 are fixed to each other only with the hot melt adhesive applied to the outer peripheral surface of the gather elastic member 63.

Similarly, for fixing the waterproof film 64 incorporated in the rising gather 60 to the gather sheet 62 and fixing the fallen portion 67, at least one of a hot melt adhesive by various application methods and a means by material welding such as heat sealing or ultrasonic sealing can be used.

The size of the rising gather 60 can be appropriately determined. However, in a case of baby applications, for example, as illustrated in FIG. 3, a rising height of the rising gather 60 (width direction length of the main unit portion 66 in an unfolded state) W2 is preferably 15 to 60 mm, and particularly preferably 20 to 40 mm. A separation distance W1 between innermost folded portions in a flatly folded state is preferably 60 to 190 mm, and particularly preferably 70 to 140 mm such that the rising gather 60 is parallel to a surface of the top sheet 30. In a case of adult applications, the rising height of the rising gather 60 (width direction length of the main unit portion 66 in an unfolded state) W2 is preferably 20 to 60 mm, and particularly preferably 30 to 55 mm. A separation distance W1 between innermost folded portions in a flatly folded state is preferably 110 to 190 mm, and particularly preferably 120 to 150 mm such that the rising gather 60 is parallel to a surface of the top sheet 30.

<Evaluation of Various Characteristics>

On the basis of the structure of the outer member separated type underpants-type disposable diaper illustrated in FIGS. 1 to 11, samples were manufactured with the size of each portion changed as illustrated in Table 1. A covering property of a gluteal region and an inguinal portion, fitting of the rising gather 60, and ease of making a hand pass through the leg opening LO were evaluated in four grades of ⊚ (very good), ○ (good), Δ (ordinary), and x (poor). The evaluation results are illustrated in Table 1.

TABLE 1

|  |  | Sample 1 | Sample 2 | Sample 3 | Sample 4 |
|---|---|---|---|---|---|
| Width direction size of first portion 60A (mm) | | 10 | 10 | 10 | 15 |
| Width direction size of second portion 60B (mm) | | 30 | 30 | 30 | 45 |
| Width direction size of protruding portion (mm) | | 20 | 20 | 20 | 30 |
| Rising height W2 of rising gather 60 (mm) | | 40 | 40 | 40 | 60 |
| Back fallen portion 67B | Front-back direction size Z1 of first fixing portion AF (mm) | 50 | 50 | 30 | 50 |
| | Front-back direction size Z2 of second fixing portion AF (mm) | 120 | 30 | 80 | 120 |
| | Front-back direction size Z of protruding fixing portion CF (mm) | 110 | 110 | 50 | 110 |
| Front fallen portion 67F | Front-back direction size Z1 of first fixing portion AF (mm) | 80 | 80 | 80 | 80 |
| | Front-back direction size Z2 of second fixing portion AF (mm) | 50 | 20 | 50 | 50 |
| | Front-back direction size Z of protruding fixing portion CF (mm) | 40 | 40 | 40 | 40 |

TABLE 1-continued

|  | Sample 1 | Sample 2 | Sample 3 | Sample 4 |
|---|---|---|---|---|
| Covering property of gluteal region and inguinal portion | ⊚ | ⊚ | Δ | ⊚ |
| Fitting of rising gather 60 | ⊚ | ⊚ | Δ | ○ |
| Ease of making hand pass through leg opening LO | ○ | ○ | ○ | Δ |

\<Explanation of Terms in Specification\>

The following terms in the specification have the following meanings unless otherwise specified in the specification.

"Front-back (longitudinal) direction" means a direction connecting a ventral side (front side) and a dorsal side (back side), and "width direction" means a direction orthogonal to the front-back direction (left-right direction).

"Front surface side" means a side closer to a wearer's skin when an underpants-type disposable diaper is worn. "Back surface side" means a side far from a wearer's skin when an underpants-type disposable diaper is worn.

"Front surface" means a surface of a member closer to a wearer's skin when an underpants-type disposable diaper is worn. "Back surface" means a surface far from a wearer's skin when an underpants-type disposable diaper is worn.

"Area ratio" means the ratio of a target portion with respect to a unit area, and represents a ratio expressed by percentage, obtained by dividing the total area of a target portion (for example, holes) in a target region (for example, cover nonwoven fabric) by the area of the target region. In a form in which a large number of target portions are disposed at intervals, it is desirable to set the target region to a size that includes 10 or more target portions and to determine the area ratio. For example, the area ratio of holes can be measured according to the following procedure using, for example, a trade name VHX-1000 manufactured by KEYENCE Corporation under measurement conditions of 20 times.

(1) A sample is set to a lens having a magnification of 20, and the focus is adjusted. The position of a nonwoven fabric is adjusted such that 4×6 holes are included.

(2) The brightness of the region of the holes is specified, and the area of the holes is measured.

(3) Color extraction of "Area measurement" in "Measurement/Comment" is clicked. The portion of the holes is clicked.

(4) "Collective measurement" is clicked, "Display measurement result window" is checked, and data is stored as CSV data.

"Stretch rate" means a value obtained when a natural length is assumed to be 100%.

"Gel strength" is measured as follows. To 49.0 g of artificial urine (mixture of 2% by weight of urea, 0.8% by weight of sodium chloride, 0.03% by weight of calcium chloride dihydrate, 0.08% by weight of magnesium sulfate heptahydrate, and 97.09% by weight of deionized water), 1.0 g of a super absorbent polymer is added, and the resulting mixture is stirred with a stirrer. The gel thus generated is left in a thermohygrostat at 40° C.×60% RH for three hours. Thereafter, the temperature is returned to room temperature, and gel strength is measured with a curdmeter (Curdmeter-MAX ME-500 manufactured by I. Techno Engineering Co., Ltd.).

"Basis weight" is measured as follows. A sample or a test piece is predried and then left in a test chamber or an apparatus in a standard state (test location is at a temperature of 23±1° C. and a relative humidity of 50±2%) so as to have a constant weight. Predrying refers to causing a sample or a test piece to have a constant weight in an environment of a temperature of 100° C. Incidentally, fibers having an official moisture regain of 0.0% do not have to be predried. A sample of 100 mm×100 mm in size is cut out from a test piece having a constant weight using a template for sampling (100 mm×100 mm). The weight of the sample is measured. The weight is multiplied by 100 to calculate the weight per square meter to be used as a basis weight.

"Thickness" is automatically measured under conditions that a load is 0.098 N/cm$^2$ and a pressing area is 2 cm$^2$ using an automatic thickness meter (KES-G5 handy compression measuring program).

Water absorption capacity is measured in accordance with JIS K7223-1996 "Test method for water absorption capacity of super absorbent polymer".

Water absorption rate is "time to end point" when JIS K7224-1996 "Test method for water absorption rate of super absorbent polymer" is performed using 2 g of super absorbent polymer and 50 g of physiological saline.

"Unfolded state" means a flatly unfolded state without contraction or slackness.

The size of each portion means a size not in a natural length state but in an unfolded state unless otherwise specified.

In a case where environmental conditions in a test and a measurement are not described, the test and the measurement are performed in a test room or an apparatus in a standard state (test location is at a temperature of 23±1° C. and a relative humidity of 50±2%).

INDUSTRIAL APPLICABILITY

The present invention is applicable to an underpants-type disposable diaper.

REFERENCE SIGNS LIST

11 Liquid impervious sheet
12B Back outer member
12E Waist extended portion
12F Front outer member
12H Inner sheet layer
12S Outer sheet layer
13 Cover nonwoven fabric
17 Waist portion elastic member
18 Unnecessary elastic member 200 Inner member
201, 202 Inner and outer bonded portion
30 Top sheet
40 Intermediate sheet
50 Absorbent element
56 Absorber
58 Wrapping sheet
60 Rising gather
60A First portion
60B Second portion
62 Gather sheet
63 Gather elastic member
67B Back fallen portion
67F Front fallen portion
68 Rising portion
69 Protruding portion
69f Free edge
A1 Non-stretchable region
A2 Stretchable region
AF First fixing portion
BF Second fixing portion
CF Protruding fixing portion
H1 Full fallen region
H2 Half fallen region
L Intermediate region
LD Front-back direction
T Lower torso region
U Under-waist portion
W Waist portion
WO Waist opening

The invention claimed is:

1. An underpants-type disposable diaper comprising:
a front outer member forming at least a lower torso portion of a front body and a back outer member forming at least a lower torso portion of a back body independently, the front outer member and the back outer member being separated from each other in a front-back direction;
an inner member including an absorber extending in the front-back direction from the front outer member to the back outer member, and being bonded to the front outer member and the back outer member respectively; and
a side seal portion to which both sides of the front outer member and both sides of the back outer member are bonded to form a waist opening, and a pair of left and right leg openings,
the inner member including raising gathers that rise from both sides,
the rising gathers each including: a main unit portion having a first portion extending from both sides of a surface of the inner member toward a center in the width direction and a second portion extending from a tip of the first portion outward in the width direction; a front fallen portion and a back fallen portion formed by fixing a front end portion and a back end portion in the main unit portion to a surface of the inner member in a state of falling down, respectively; a non-fixed rising portion located between the front fallen portion and the back fallen portion; and a gather elastic member attached to at least a tip portion of the rising portion in the front-back direction,
wherein
each of the front fallen portion and the back fallen portion has a protruding portion in which the second portion protrudes 5 to 40 mm outward in the width direction than a side edge of the first portion,
the protruding portion of the front fallen portion has a protruding fixing portion fixed to the front outer member overlapping with a back surface side thereof, and the protruding portion of the back fallen portion has a protruding fixing portion fixed to the back outer member overlapping with a back surface side thereof;
the front fallen portion and the back fallen portion each have a first fixing portion in which the first portion is bonded to a surface of the inner member, and a second fixing portion in which the second portion is bonded to the first portion, and
the back fallen portion further has a full fallen region having the first fixing portion and the second fixing portion on a back side, and has a half fallen region not having the first fixing portion and having the second fixing portion on a front side, and a front-back direction size of the second fixing portion is at least twice a front-back direction size of the first fixing portion..

2. The underpants-type disposable diaper according to claim 1, wherein
the front fallen portion has a full fallen region having the first fixing portion and the second fixing portion on a front side, and has a half fallen region not having the second fixing portion and having the first fixing portion on a back side.

3. The underpants-type disposable diaper according to claim 1, wherein
a front-back direction size of the protruding fixing portion in the back fallen portion is 0.7 to 1 time a size of a longer one out of a front-back direction size of the first fixing portion and a front-back direction size of the second fixing portion located on a lateral side thereof, and
a front-back direction size of the protruding fixing portion in the front fallen portion is 0.7 to 1 time a size of a shorter one out of a front-back direction size of the first fixing portion and a front-back direction size of the second fixing portion located on a lateral side thereof.

4. The underpants-type disposable diaper according to claim 2, wherein
a side edge portion of the protruding portion is a non-fixed free edge,
a gather elastic member disposed at a tip portion of the rising portion extends to the free edge, and
the free edge rises by contraction of the gather elastic member.

5. The underpants-type disposable diaper according to claim 1, wherein
the front outer member and the back outer member each have a stretchable region that stretches and contracts in a width direction in a portion overlapping with the protruding portion, and
the protruding fixing portion of the front fallen portion is fixed to the stretchable region of the front outer member, the protruding fixing portion of the back fallen portion is fixed to the stretchable region of the back outer member, and the protruding fixing portions are stretchable together with the stretchable regions.

6. The underpants-type disposable diaper according to claim 5, wherein the protruding fixing portion does not contract by contraction of the gather elastic member.

7. The underpants-type disposable diaper according to claim 1, wherein
the back fallen portion is disposed on a front edge of the back outer member or on a back side thereof, and the front fallen portion is disposed on a back edge of the front outer member or on a front side thereof.

8. The underpants-type disposable diaper according to claim 2, wherein
- a front-back direction size of the protruding fixing portion in the back fallen portion is 0.7 to 1 time a size of a longer one out of a front-back direction size of the first fixing portion and a front-back direction size of the second fixing portion located on a lateral side thereof, and
- a front-back direction size of the protruding fixing portion in the front fallen portion is 0.7 to 1 time a size of a shorter one out of a front-back direction size of the first fixing portion and a front-back direction size of the second fixing portion located on a lateral side thereof.

9. The underpants-type disposable diaper according to claim 3, wherein
- a side edge portion of the protruding portion is a non-fixed free edge,
- a gather elastic member disposed at a tip portion of the rising portion extends to the free edge, and
- the free edge rises by contraction of the gather elastic member.

10. The underpants-type disposable diaper according to claim 2, wherein
- the front outer member and the back outer member each have a stretchable region that stretches and contracts in a width direction in a portion overlapping with the protruding portion, and
- the protruding fixing portion of the front fallen portion is fixed to the stretchable region of the front outer member, the protruding fixing portion of the back fallen portion is fixed to the stretchable region of the back outer member, and the protruding fixing portions are stretchable together with the stretchable regions.

11. The underpants-type disposable diaper according to claim 3, wherein
- the front outer member and the back outer member each have a stretchable region that stretches and contracts in a width direction in a portion overlapping with the protruding portion, and
- the protruding fixing portion of the front fallen portion is fixed to the stretchable region of the front outer member, the protruding fixing portion of the back fallen portion is fixed to the stretchable region of the back outer member, and the protruding fixing portions are stretchable together with the stretchable regions.

12. The underpants-type disposable diaper according to claim 4, wherein
- the front outer member and the back outer member each have a stretchable region that stretches and contracts in a width direction in a portion overlapping with the protruding portion, and
- the protruding fixing portion of the front fallen portion is fixed to the stretchable region of the front outer member, the protruding fixing portion of the back fallen portion is fixed to the stretchable region of the back outer member, and the protruding fixing portions are stretchable together with the stretchable regions.

13. The underpants-type disposable diaper according to claim 2, wherein
- the back fallen portion is disposed on a front edge of the back outer member or on a back side thereof, and the front fallen portion is disposed on a back edge of the front outer member or on a front side thereof.

14. The underpants-type disposable diaper according to claim 3, wherein
- the back fallen portion is disposed on a front edge of the back outer member or on a back side thereof, and the front fallen portion is disposed on a back edge of the front outer member or on a front side thereof.

15. The underpants-type disposable diaper according to claim 4, wherein
- the back fallen portion is disposed on a front edge of the back outer member or on a back side thereof, and the front fallen portion is disposed on a back edge of the front outer member or on a front side thereof.

16. The underpants-type disposable diaper according to claim 5, wherein
- the back fallen portion is disposed on a front edge of the back outer member or on a back side thereof, and the front fallen portion is disposed on a back edge of the front outer member or on a front side thereof.

17. The underpants-type disposable diaper according to claim 6, wherein
- the back fallen portion is disposed on a front edge of the back outer member or on a back side thereof, and the front fallen portion is disposed on a back edge of the front outer member or on a front side thereof.

* * * * *